United States Patent [19]

Houck et al.

[11] Patent Number: 5,177,307
[45] Date of Patent: Jan. 5, 1993

[54] COMPOSITIONS AND METHODS FOR MODULATION OF ENDOGENOUS CYTOKININ LEVELS

[75] Inventors: Catherine M. Houck, Vacaville; Julie R. Pear, Davis; Belinda M. Martineau, Davis; William Hiatt, Davis, all of Calif.

[73] Assignee: Calgene, Inc., Davis, Calif.

[21] Appl. No.: 554,196

[22] Filed: Jul. 17, 1990

Related U.S. Application Data

[63] Continuation-in-part of Ser. No. 382,802, Jul. 19, 1989, abandoned, which is a continuation-in-part of Ser. No. 188,361, Apr. 29, 1988, abandoned, which is a continuation-in-part of Ser. No. 168,190, Mar. 15, 1988, abandoned, which is a continuation-in-part of Ser. No. 54,369, May 26, 1987, Pat. No. 4,943,674.

[51] Int. Cl.⁵ .................... A01H 1/04; C12P 21/06; C12N 15/00; C12N 5/00; C12N 9/00; C07H 15/12
[52] U.S. Cl. .................... 800/205; 800/DIG. 44; 435/69.1; 435/70.1; 435/172.3; 435/183; 435/240.4; 435/320.1; 536/23.6; 536/24.1; 935/35; 935/36; 935/64; 935/67
[58] Field of Search .............. 435/69.1, 172.3, 240.4, 435/320.1, 183, 70.1; 800/205, DIG. 44; 935/35, 36, 64, 67; 536/27

[56] References Cited

U.S. PATENT DOCUMENTS 4,801,540 1/1989 Hiatt et al. .................... 435/172.3
4,943,674 7/1990 Houck et al. .................... 800/205

FOREIGN PATENT DOCUMENTS 0344029 4/1989 European Pat. Off.
88/09334 5/1988 World Int. Prop. O.

OTHER PUBLICATIONS

Facciotti et al. 1985, Bio/Technol. 3(3): 241-246.
Larkins et al. 1985, J. Cell. Biochem. Suppl. 90:264.
Murai et al. 1983, Science 222:476-482.
Wands (USPQ2d) 1400 (Fed. Cir. 1988).
Sargent et al.; "Isolation of Differentially Expressed Genes"; Methods in Enzymology (1987) 152:423-432.
McCormick et al.; "Identification of Genes Specifically Expressed in Reproductive Organs of Tomato"; Tomato Biotechnology; (1987) pp. 255-265.
Beachy et al. "Accumulation and Assembly of Soybean β-Conglycinin in Seeds of Transformed Petunia Plants"; EMBO Journal; vol. 4, No. 12, pp. 3047-3053 (1985).
Rogers et al.; "Gene Transfer in Plants: Production of Transformed Plants Using Ti Plasmid Vectors"; Methods in Enzymology; vol. 118, pp. 627-641 (1986).
Klee, H. J. and Medford, J. I., "Manipulation of Endogenous Auxin and Cytokinin Levels in Transgenic Plants" J. of Cellular Biochemistry 12C:152 (1987).
Twell, D., et al., "Pollen-Specific Expression Directed by Chimaeric Genes in Transgenic Tomato and Tobacco Plants": J. of Cellular Biochemistry 13D:312 (1989).
Gasser, C. S., et al., "Isolation of tissue specific cDNAs from tomato pistils" The Plant Cell 1:15-24 (1989).
Twell, D., et al., "Isolation and expression of an anther-specific gene from tomato" Mol. Gen. Genet 217:240-245 (1989).
Medford et al., "Alterations of Endogenous Cytokinins in Transgenic Plants Using a Chimeric Isopentenyl Transferase Gene," The Plant Cell (1989) 1:403-413.
Sturtevant and Taller, "Cytokinin Production by Bradyrhizobium japonicum," Plant Physiology (1989) 89:1247-1252.
Memelink et al., "Changes in the tissue-specific preva- (List continued on next page.)

Primary Examiner—David T. Fox
Attorney, Agent, or Firm—Barbara Rae-Venter

[57] ABSTRACT

Developmentally regulated transcriptional regulatory regions are identified employing cDNA screening. The resulting regulatory regions are manipulated for use with DNA sequences encoding enzymes involved in cytokinin metabolism for introduction into plant cells to provide transformed plants having tissue, particularly fruit, with a modified phenotypic property.

17 Claims, 8 Drawing Sheets 2613-4 DATA

OTHER PUBLICATIONS lence of translatable mRNAs in trangenic tobacco shoots containing the T-DNA cytokinin gene," *Plant Molecular Biology* (1988) 11:625-631.

Davey and Van Staden, "Endogenous Cytokinins in the Fruits of Ripening and Non-Ripening Tomatoes," *Plant Science Letters* (1978) 11:359-364.

Dilley, "Hormonal Control of Fruit Ripening," *HortScience* (1969) 4(2):11-14.

Van Staden and Cook, "Cytokinins and Fruit Production," *Acta Horticulture* (1986) 179:73-81.

DellaPenna et al., "Molecular Cloning of Tomato Fruit Polygalacturonase: Analysis of Polygalacturonase mRNA Levels During Ripening," *Proceedings of the National Academy of Sciences USA* (1986) 83:6420-6424.

Grierson et al., "Sequencing and Identification of a cDNA Clone for Tomato Polygalacturonase," *Nucleic Acids Research* (1986) 14:8595-8603.

Slater et al., "Isolation and Characterization of cDNA for Tomato Polygalacturonase and Other Ripening Related Proteins" *Plant Molecular Biology* (1985) 5:137-147.

Smith et al., "Rapid Appearance of an mRNA Correlated With Ethylene Synthesis Encoding a Protein of Molecular Weight 35000" *Planta* (1986) 168:94-100.

Mansson et al., "Characterization of Fruit-Specific cDNAs from Tomato," *Molecular and General Genetics* (1985) 200:356-361.

Graham et al., "Wound-Induced Proteinase Inhibitorse from Tomato Leaves, I and II," *Journal of Biological Chemistry* (1985) 260:6555-6564.

Desai & Chism, "Changes in Cytokinin Activity in Ripening Tomato Fruit," *J. Food Sciences* (1978) 43:1324-1326.

McCormick et al., "Leaf disc transformation of cultivated tomato (*L. esculentum*) using *Agrobacterium tumefaciens*," *Plant Cell Reports* (1986) 5:81-84.

Piechulla et al., "Expression of nuclear and plastid genes for photosynthesis-specific proteins during tomato fruit development and ripening," *Plant Molecular Biology* (1986) 7:367-376.

Akiyoshi et al., "T-DNA of *Agrobacterium tumefaciens* encodes an enzyme of cytokinin biosynthesis," *Proceedings of the National Academy of Sciences USA* (1984) 81:5994-5998.

Barry et al., "Identification of a cloned cytokinin biosynthetic gene," *Proceedings of the National Academy of Sciences USA* (1984) 81:4776-4780.

Akiyoshi et al., "Cytokinin/auxi balance in crown gall tumors is regulated by specific loci in the T-DNA," *Proceedings of the National Academy of Sciences USA* (1983) 80:407-411.

Adel-Rahman, "Patterns of Hormones, Respiration and Ripening Enzymes during Development, Maturation and Ripening of Cherry Tomato Fruits," *Physol. Plant* (1977) 39:115-118.

Varga and Bruinsma, "The growth and ripening of tomato fruits at different levels of endogenous cytokinins," *Journal of Horticultural Science*, (1974) 49:135-142.

Abdel-Kader et al., "Effect of Growth-Regulation Substances on the Ripening and Shelf-Life of Tomatoes," *HortScience* (1966) 1:90-91.

Smigocki, A. C., et al., "Cytokinin gene fused with a strong promoter enhances shoot organogensis and zeatin levels in transformed plant cells" *Proc. Natl. Aca. Sci.* 85:5131-5135 (1988).

Bird, C. R. et al., "The tomato polygalaturonase gene and ripening-specific expression in transgenic plants" *Plant Molecular Biology*, 11:651-662 (1988).

Hiatt, W. R. et al., "Expression of selected genes during tomato fruit maturation and ripening" *J. Cell Biochem. Supp. O*: 148 (1988).

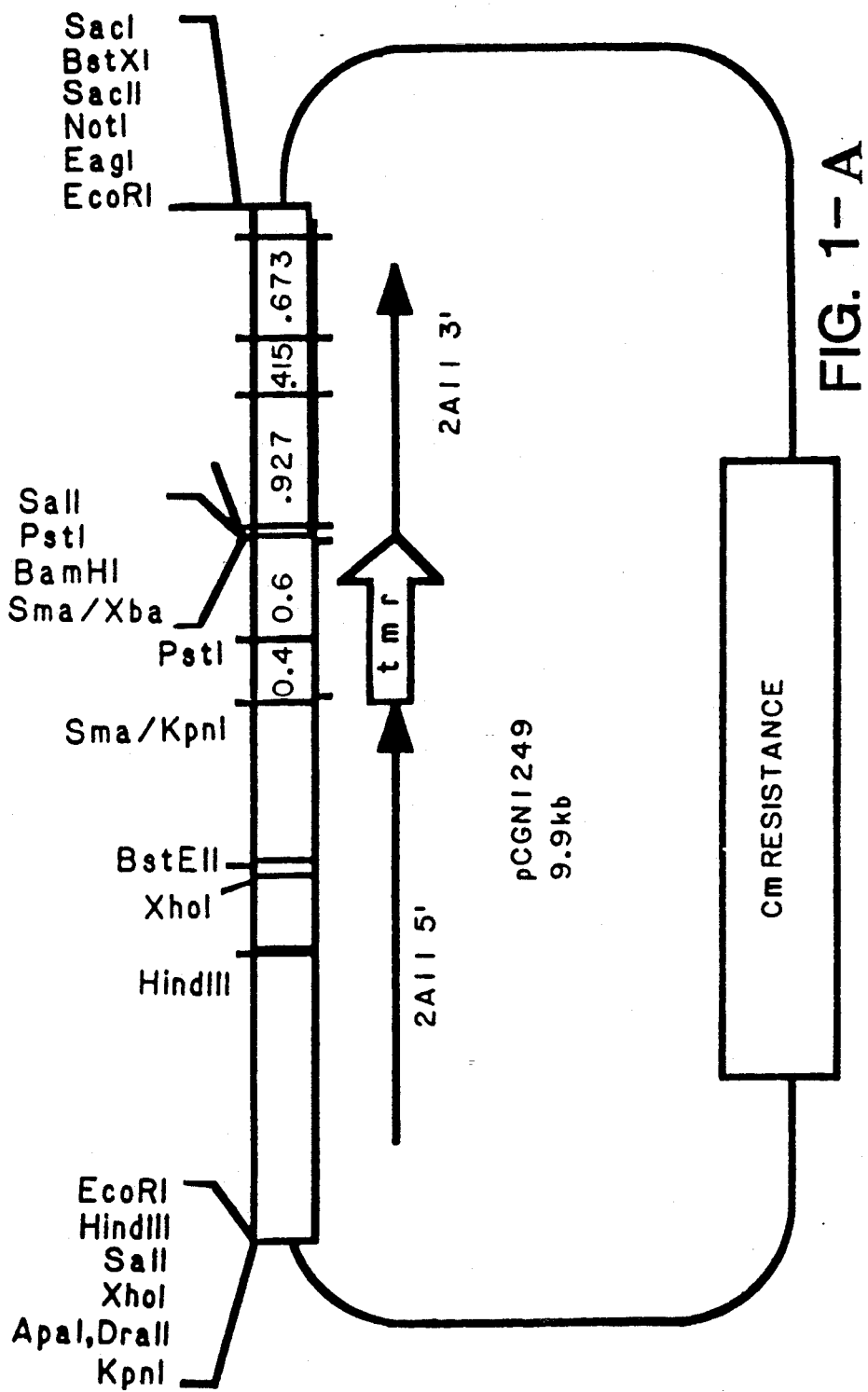
FIG. 1-A

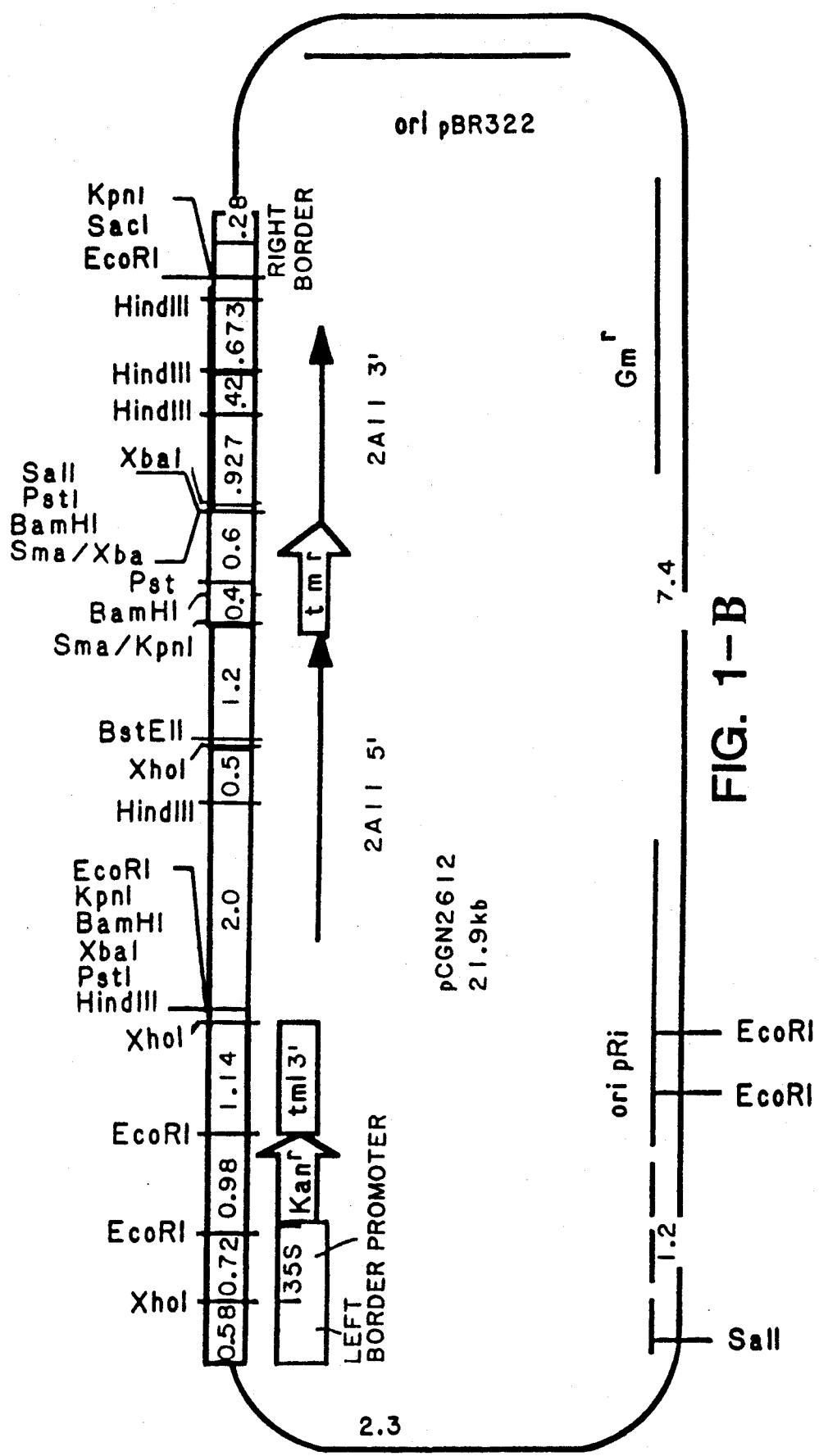
FIG. 1-B

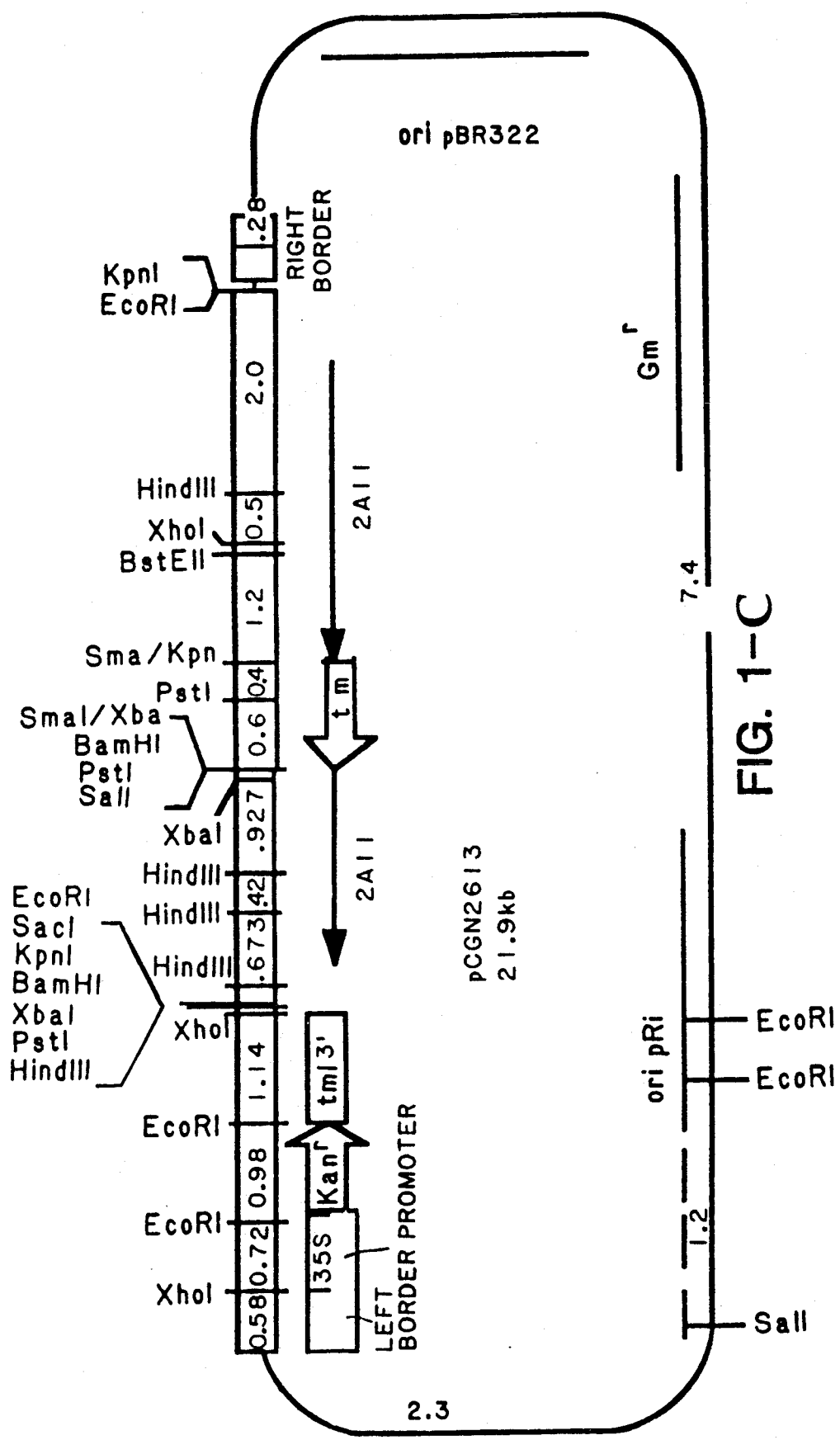
FIG. 1-C

```
   1 GCTCCACTACTACTCTCATCACTTAGTCATCAAGCCTTCTTTATACCAA        49
  50 GGCATCATCAATCTCATTAACAAAGTAGATTAGGGTTTTCAAGATTTA         98
  99 GGATTCAATAGCTTCATCATGCTTATTTATCACAATTATAATCACA          147
 148 TTCATACAAGCATACATTAAGCATATAGAAGGGTTTACAATACTACCC        196
 197 AATACATATCATTCGCTATTAAGAGTTTACTACGAATAGCATAAACCAT       245
 246 AACCTACCTCCACCGAAGAATCGCGATCAAACAATCTACTTTCCCAAAG       294
 295 CTGCGTTCTTCTTCGTTTCTCTCTTTCTCCTTGATCGTTCTTCCCTC         343
 344 TCTTTGTTCTTTCTTCTATTTTTCTATTCAAACCCTCTTTCTTTTACCCTA     392
 393 ATTAGTATATAATTAAGTATAAAAGATGATAAAATACCCCATCTATTTG       441
 442 TTTGAAGGTTATCTCTTTTAGCCCCCAAGTAATTGAATTATTAACATTA       490
 491 AACCACTAACTTTATAATTATAGCAGGAATAGTCCAAAAGCCCCTTA         593
 540 AAATATTTAACAGAAATCCGACCCAGTCCTGCAGGTGCAGCCTGTANCG       588
 589 GNNCACAACTGTGACGGTCCGTCCTGCATGGCCGTCACAAAGTTCAGAG       637
 638 AGTTAATTTCTGTGGAAGATGTANGGTNGTCGTGCCCACGACGTCC          686
 687 GTCCTGTCATTTCGTTACGAAGTTCAGAGAGTCGATTTCAGTACCCAAA       735
     EcoRI
     ————
 736 TTTCAGAATTCTAAGTGTTTTGGAACGAGACCCCNCGGTCCGTCGTGCC       784
     BamHI  SalI
     ————   ————
 785 CATGACGGTTCGTCGTCGGGATCCGTCGTCGACTCAGCCAGTTTTCCAAAAT    833
 834 TAAAATCTGCTGCTCAAAACGACTAAACAGGTCGTTACAAAGTACTCAA       882
 883 TCAAATAAAAAGAATAAATTCTTTTCCAAATACATATATTGTTTATAGG       931
 932 ACAGTGTTAACAGGGAAATGTAATCGTTGCCTCAATCGATTTTTTTT         980
     BglII
     —————
 981 TGAAATTAAGATTGATTAGATCTTCTTTAAGATAACAATGTCTCAAAGA       1029
1030 TAAATTGAATGAATGAATTAGCTATATTATCATTTGAAAAGAAATTACT       1078
1079 AAAACAGATTGATAATAAAATAATAATAAATGACTTTGCATCTAAAATA       1127
```

FIG. 3-A

```
1128  GCTAGAAAGCAGATTTTTAAATAAAAATACATATGATAAAAAAGATA  1176
1177  AATTAGAGTCATCCCATAAATTTCGCTTTAGCCCCAATGTTGTTAAG  1225
1226  TCGGCCCTGAAAATAGGAATGGTATTAAATATTTTGTTTTGATTTCACA 1274
1275  CTTGATATTTGACATTCATATTAGAAAATAATTAAATTATATTCGTGT  1323
1324  AGAGTGGTCTCACATTAATGGGTAAATATATTCCACACAAAACTATTT  1372
1373  TACAATCATAGCTAGAATCTGAAATATCTAATGTACTCCACCAATTAA  1421
1422  TTAAAGATGATTTTTTGCTTAAATAATAATATGTCTATTGCCAAA     1470
1471  CTACTAATAGATAGTACTCACAAAAAATAAAATAAAAATCAAGTGTA   1519
1520  TATACAATGATTCGGAAGGCCATTTTGAAATTTTCATAAAATGACCG   1568
1569  TTTTACCCGTTCACAATTGTGTTTCAGCATTTTGTTTGGTTTGTGGA   1617
                                     HindIII
1618  TTTGGTTATGGAAGTTCAATAAAAAAGTTGTGGTTTTATAAGCTTTGGAG 1666
1667  TTTGAAAGGTTTAAGTTGATTAAAAGTTTTAGTGTCAATTGGAG       1715
1716  TTTCGTGTCTTGAAATAAATTTATCACTTGCATTAGTTTCAAATGTC    1764
1765  GAGTTTGGTTAAGTAGAGAGTTTTTTCATTCGGAGTTTTTTATGAATT   1813
1814  TAAAATGTTAAGCTGAAAGTTTATGAGAAATTTTTTGAGTTAATTT     1862
1863  TGATGCTTGAATTAAATTTTTGAGAATTTTTTGAAATCTGGGGATAAT   1911
1912  GTTAGGTCTTAGAGAAGTCTGGTTGAATTTCATAGCTCAAGAGATTAG   1960
1961  TTTTGACTTTTTAGGCATTTGTTGGTTTATTACGATTTTCACGGACTT   2009
2010  TCGAATTAAGGAGACTTCAAAATTCATATTAATGGTTCGTGTGTTCGT   2058
2059  TAGTTTTAAAAATCGTGTCTTATACATGTAATTCTGTCATAAGATAAGGTTGT 2107
2108  ATAAAATAAAGTACTACTAACATGTAAATTCATAAAATAAAAAAGTAAGGTTGT 2156
2157  ACATTAGGACTATTTGAATATTCATCAAAATAAAAAAGTAGAGAT      2205

2206  GATAGTAATATAAATATTTATTTTGATTTTACATTGATATTTTAATA    2254
2255  CTAACAATATGACATAATAAATTGTATTCAGATTGTAAAATATTCCC    2303
2304  TAAAAAAGATACTTTTACTGTGGTGGCTCAAATTCAAATTTTCTAAG    2352
```

```
2353 AAAAACTACTAATAATTGATTTCTAATTAAAATTTCGATATATATATAT 2401
2402 ATATATATATATATTTTTACTTCATTAATATACTTCACCTACCTCAATTATTATTA 2450
2451 TTTCTTTTTTTTTACTTCACATATTTTGGSCSACCAATTTTTTTT 2499
2500 TAACTTTTTGGTCTTACTCTTATTTCACTCCCTATAAATAACTCCCAT 2548
2549 TGTGTGATATTTTATTCAcAACTCTAACTTACAATCTTTCTTATTATT 2597
                          NcoI
                          ─────
2598 AAAAAAAACAAAAACATTTCTAATCTTTTCACTCATTCCATGGCTCGT 2646
2647 TCCATTTTCTCATGGCATTTTGGTCTTGGCAATGATGCTCTTTGTTA 2695
2696 CCTATGgtttgtcttcataattattcctctaaatcatcgcaataaaa 2744
2745 aaaaatgtaacgaagcagacatcagtaaaccgtttaaataaccctaa 2793
2794 aaaaattgtgaattgatattactgctatacgtttaacaactatgataa 2842
2843 aaaaccctaaaatatacttattcgatttcgtctctcatgttattc 2891
2892 taactatttttgtgtgtgaatgattgtagAGGTAGAAGCTCAGCAAAT 2940
2941 TTGCAAAGCACCAAGCCAAACTTCCCAGGATTATGTTTATGGACTCA 2989
2990 TCAATGTAGAAAATATTGTATCAAAGAGAAATTTACTGGTGTGTA 3038
3039 GCAAACTCCAAGTGAAGTTCTATGCACTAAGCCATGTGAGGAAGCAAAACTCTA 3087
3088 AATCTCAAGTGAAGTTGCTTGAAGAAGAGATTATGATGGAGTAATAATTAAGTG 3136
3137 AGTGAAGTTGTGCTTGAAGGATTTTGAGTGGTAGCATTAAATAAGTTGTCAAAAAAACAAATAATAAAAGTG 3185
3186 AGGTTAAATAAGGATTTTGAGTGGTAGCATTAAATAAGTTTGTGACACATGTAATTAATCC 3234
3235 TTGCCTTTTCTTATTGGTGTGTTAGTTTAGACACATCATTAATCC 3283
3284 ATAGTAGCCATTTGACACATTAAATAAGTTTGTGACACATCATTAATCC 3332
3333 TTATGTATGATGTTTAATGAAAATGATCGACTACGATCTTTAATTT 3381
3382 TATGTTTACATTAATTAATCACTTTCTGTTACGATTCATTATCTAG 3430
3431 TTATGAATGAAATAGAGTGATTTGAAGTAAGGAGCTAGTCTTCAAAC 3479
3480 AAAGACGTACATATGTACAAAGTAGGGTACTATTAAACTTCTTTTTAT 3528
```

```
3529  GATTCGATATATTCATATTTGATACTCAAATTAGAGTTAAATTCATATT  3577
3578  AATTTGTACGAGAGAAATTTAAACTATAATAAATAAAACTCCCTAATAAA  3626
                                  EcoRI
                                  |
3627  AGATTACTTTCATGATAGAATATATATATATTGAATTCTTGTTGCTGA  3675
3676  ATTTATATTATGGTCATGCAAAACTTAGGAAAATAAAATGAAAGATAAA  3724
3725  TAATATGTGCTTGATGACAACTTTATGCCTGAATTAATATAATAATAAT  3773
3774  TAATATAAAATGATGAATTAATAATACTTTATAATAAGTTTTTTCTTCA  3822
3823  TCATTTGAATCTATTGAATGGTATTAAACATTTTATTTGATTTTACAT  3871
3872  TCGATATTTGATATTTATAATAGAAAATGATTAAATTTATATTCGTTTA  3920
3921  GAGAGGTCTCATATTAAAGGATAAAAATATCTAATAAAAGTTACTTT  3969
3970  ACAATCATAGTTAAAATCTGAAATATCTAATGTTGTAATGACCCGATAG  4018
4019  ATTATTTTGGGAATTTAAACTATTGCTTAACTTAAGTTAATTAATT  4067
4068  CATGAATAATTATAGATAATTGACTTAATCAATAGTTAATGATACAACT  4116
4117  ATATACTATTTGACCCTTATAATGTTGTGTTAAATATTGGTCTTTAGTA  4165
4167  GCCATTTGACACATTAAATAAGTATTGCATAAATATTCATGAGCTAAAA  4215
4216  ATCAATTAGAATCATATCAGTAAATATTCAATTCATCGATTTTGCAAAA  4264
4265  AAAATTGAAAAAAAATTAAACAATTGCACACATCCATCAATTTAAGCATTAAG  4313
4314  TTATGCAGAAAAATTAAACAATTGCACACATCCATCAATTTAAGCATTAAG  4362
                                BamHI
                                |
4363  TATTTAGCCCCTCTCTTGGATCC  4384
```

FIG. 3-D ns and novel DNA constructions are provided for modulating cytokinin levels in plant cells, particularly fruit. Expression cassettes comprising a DNA

COMPOSITIONS AND METHODS FOR MODULATION OF ENDOGENOUS CYTOKININ LEVELS

CROSS-REFERENCE TO RELATED APPLICATIONS

This application is a continuation-in-part of application Ser. No. 382,802, filed Jul. 19, 1989, now abandoned, which is a continuation-in-part of application Ser. No. 188,361, filed Apr. 29, 1988, now abandoned, which is a continuation-in-part of application Ser. No. 168,190, filed Mar. 15, 1988, now abandoned, which is a continuation-in-part of application Ser. No. 054,369 filed May 26, 1987, now U.S. Pat. No. 4,943,674, which applications are incorporated herein by reference.

INTRODUCTION

1. Technical Field

This invention relates to methods and compositions for modulating cytokinin levels by expressing genes encoding enzymes involved in the metabolism of cytokinins, particularly in fruit so as to control fruit development, maturation and ripening.

2. Background

In general, genetic engineering techniques have been directed to modifying the phenotype of individual prokaryotic and eukaryotic cells, especially in culture. Plant cells have proven more intransigent than other eukaryotic cells due not only to the lack of suitable vector systems but also as a result of the different goals involved. For many applications, it is desirable to provide for transcription of a gene of interest in a particular plant tissue and/or at a particular time in the development of the plant or maturation cycle of the tissue. Toward this end, there is a substantial interest in modulating expression of endogenous plant products involved in the quality and/or ripening of fruit. Plant products of particular interest include those which may be involved in a variety of physiological developments, including changes in cell size and cell number as well as differentiation.

In some instances, where it is desirable to increase the level of the endogenous plant product in a tissue of interest, elevated levels of the particular plant product may be deleterious to tissues other than the tissue of interest, for example, fruit. It is therefore desirable to restrict expression to the tissue of interest. Alternatively, expression of the plant product at other than a particular time in the tissue of interest may be deleterious or have no utility (for example, a time in development when the tissue is refractory to the effects of the plant product), so that energy of the plant is wasted, reducing growth potential. It is therefore of interest to identify appropriate promoter sequences which will provide for the desired timing and tissue specificity of expression of the plant product. One aspect of this interest is the ability to modulate the ripening process of fruit so as to provide fruit having improved aspects for storage, handling, cooking, organoleptic properties, freezing, nutritional value, and the like. Another aspect of this interest is the ability to increase the number of cells at an early stage in fruit development so as to provide for an increase in solids in the mature tissue, particularly fruit.

RELEVANT LITERATURE

Increased synthesis of cytokinins in plants transformed with a chimeric gene comprising a DNA sequence encoding isopentenyl transferase (ipt), also known as DMA transferase encoded by the tmr locus from *A. tumefaciens*, and the heat inducible maize hsp70 promoter has been reported. Medford et al., *The Plant Cell* (1989) 1:403-413. Smigocki et al., *Proc. Nat'l. Acad. Sci. USA* (1988) 85:5131-5135 have disclosed chimeric gene constructs comprising a DNA sequence encoding ipt and either the 35S or the NOS promoter. Shoot organogenesis and zeatin levels were reportedly enhanced in plant cells transformed with the 35S construct. Articles relating to the role of cytokinins in fruit ripening and/or maturation include the following: Desai et al., *J. Food Science* (1978) 43:1324-1326; Davey et al., *Plant Science Letters* (1978) 11:359-364; Dilley, *HortScience* (1969) 43:11-14.

cDNA clones from tomato displaying differential expression during fruit development have been isolated and characterized. Mansson et al., *Mol. Gen. Genet.* (1985) 200:356-361; Slater et al., *Plant Mol. Biol.* (1985) 5:137-147. The studies have focused primarily on mRNAs which accumulate during fruit ripening. One of the proteins encoded by the ripening-specific cDNAs has been identified as polygalacturonase. Slater et al., *Plant Mol. Biol.* (1985) 5:137-147. A cDNA clone which encodes tomato polygalacturonase has been sequenced. Grierson et al., *Nucleic Acids Research* (1986) 14:8395-8603. The concentration of polygalacturonase mRNA increases 2000-fold between the immature-green and red-ripe stages of fruit development. This suggests that expression of the enzyme is regulated by the specific mRNA concentration which in turn is regulated by an increase in transcription. Della Penna et al., *Proc. Nat'l. Acad. Sci. USA* (1986) 83:6420-6424. Mature plastid mRNA for psbA (one of the components of photosystem II) reaches its highest level late in fruit development, whereas after the onset of ripening, plastid mRNAs for other components of photosystem I and II decline to nondetectable levels in chromoplasts. Piechulla, et al., *Plant Mol. Biol.* (1986) 7:367-376.

Other studies have focused on cDNAs encoding genes under inducible regulation, e.g., proteinase inhibitors which are expressed in response to wounding in tomato (Graham et al., *J. Biol. Chem.* (1985) 260:6555-6560; Graham et al., *J. Biol. Chem.* (1985) 260:6561-6564) and on mRNAs correlated with ethylene synthesis in ripening fruit and leaves after wounding. Smith et al., *Planta* (1986) 168:94-100.

Leaf disc transformation of cultivated tomato is described by McCormick, et al., *Plant Cell Reports* (1986) 5:81-89.

SUMMARY OF THE INVENTION

Methods and novel DNA constructions are provided for modulating cytokinin levels in plant cells, particularly fruit. Expression cassettes comprising a DNA sequence encoding an enzyme in cytokinin metabolism ("cytokinin gene") under the transcriptional control of a promoter functional in a plant cell, particularly a promoter active in a particular tissue and/or active at a specific stage in the development of a plant of interest and a transcriptional termination region are introduced into a host plant cell for integration into the genome and transcription of the cytokinin gene as provided by the promoter region. In this manner, cytokinin concentrations can be modulated in a tissue of interest and/or at a period of interest during development of the host plant. Control of cytokinin concentrations can be used, for example, to increase solids in fruit and to delay senescence.

BRIEF DESCRIPTION OF THE DRAWINGS

FIGS. 1A–1C show a map of plasmids pCGN1249 (FIG. 1-A), pCGN2612 (FIG. 1-B) and pCGN2613 (FIG. 1-C).

FIGS. 3A–3D show a complete sequence of the region of Calgene λ140 genomic clone that overlaps with the pZ130 cDNA clone (this region is underlined) and a partial sequence of regions 5' and 3' to that region. The start of the pZ130 gene transcript is indicated by the underlined, boldfaced (A) at position 2567. An intron in the gene sequences is indicated by the lower case sequence from position 2702 through position 2921. Sites for common restriction enzymes are indicated. It is possible that small gaps in the sequence may exist upstream from the SaII site bound at position 808.

Figure 2:
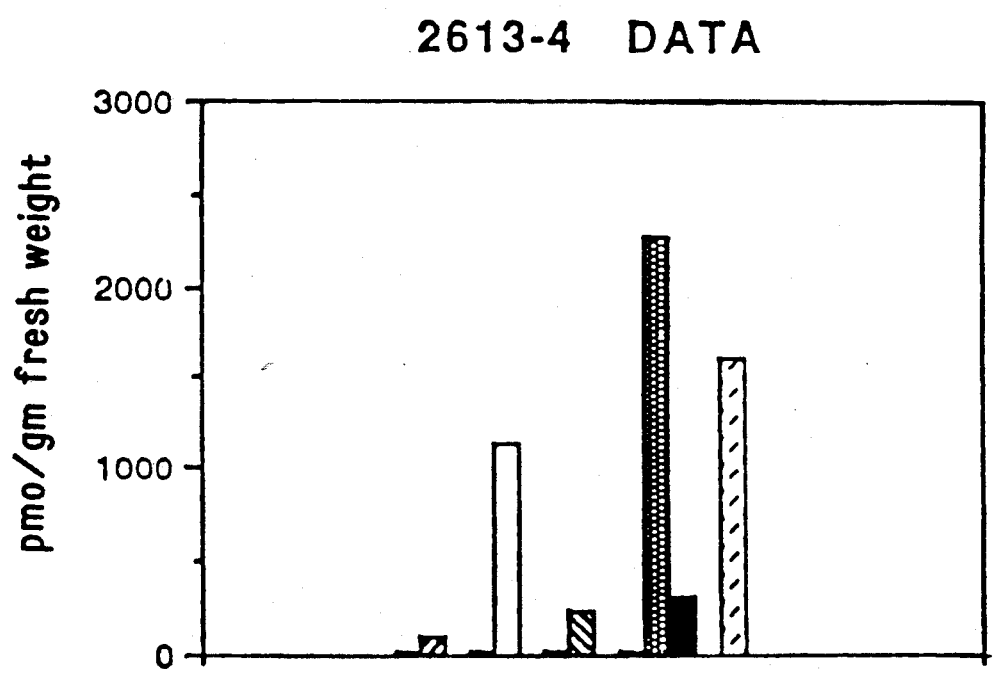
FIG. 2 shows levels of zeatin riboside in tissues collected from tomato plants transformed with plasmid pCGN2613 (i.e. testing positive for kanamycin resistance; kan+) and those collected from "null" siblings of the transformed plants (individuals lacking kanamycin resistance; i.e. not containing pCGN2613). Bars represent (from left to right): null plant leaves; kan+ plant leaves; young green fruit from null plant; young green fruit from kan+ plant; older green fruit from null plant; older green fruit from kan− plant; ripe fruit from null plant; red "patches" from "ripe" fruit of kan+ plant; green "patches" from "ripe" fruit of kan+ plant; A. tumefaciens strain C58-induced gall tissue.

The symbols in the sequence have the following meaning: A=adenosine, C=cytosine, G=guanine, T=tyrosine or uracil, R=A or G, Y=C or T or U, M=C or A, K=T or U or G, W=T or U or A, S=C or G, N=either C, T, A, G or U, B=not A, D=not C, H=not G, V=not T or U.

DESCRIPTION OF THE SPECIFIC EMBODIMENTS

Methods and compositions are provided which allow for modification of plant phenotype by modifying cytokinin levels during a specific time and/or in specific tissue(s) during the development of a plant. The method involves introducing an expression cassette comprising a developmentally regulated transcriptional initiation region joined upstream from a DNA sequence encoding an enzyme in cytokinin metabolism ("cytokinin gene") into a plant cell host; "metabolism" is intended to include both synthesis and degradation. Desirably, the cassette is integrated into the genome of a host plant cell. Conveniently, the expression cassette may also include a multiple cloning site upstream from the cytokinin gene so that the integration construct may be employed with a variety of transcriptional initiation regions depending upon the desired timing or tissue specificity for expression of the cytokinin gene.

Modulation of cytokinin concentrations can be used to modify a number of aspects of plant phenotype. Of particular interest to modify are tissue specific characteristics, such as those relating to handling of botanical fruit, for example, the total solids content of ripe fruit, improved retention of early fruit, and time of onset of ripening. According to the subject invention, such characteristics can be modified by tissue-specific modulation of plant products involved in development of the plant, particularly cytokinins, at a particular time in plant development. Cytokinins are considered to play a major role in, for example, cell division, cell enlargement, cell differentiation, bud dormancy, rooting, nutrient mobilization, as well as retardation of senescence.

The concentration of cytokinins typically does not remain constant during plant development, and the absolute concentration of the cytokinins in a given tissue may not be dispositive of a physiological effect; rather the cytokinins may act only on tissue rendered competent by other cell factors during a certain phase of development, and/or they may need to be present in concert with other cell factors such as auxins and gibberellins in a particular ratio. Thus, in order to obtain a biological response to the modulated cytokinin concentration, it may be necessary to obtain transcription or expression of the cytokinin gene only at particular stages of interest during development. It will be necessary to identify other cellular products that appear during the period of interest, preferably in the tissue of interest, such as fruit, for example, tomato or cotton roots with respect to auxin/cytokinin "rooting" and "shooting" ratios in plants, for example, to increase root mass; leaf, for example, tobacco lettuce or petunia; or seeds, for example, rapeseed or soybean; and to demonstrate their absence at other times or in other tissue, identify nucleic acid sequences associated with the cellular products and then identify the sequences in the genome of the plant in order to obtain the 5'-untranslated sequences associated with transcription. Fruit growth, development and maturation after anthesis can be divided into three major stages: a period of cell division characterized by a slow increase in both weight and size of fruit; a period of cell enlargement characterized by sharp increases in the weight and size of the fruit, during which the seed develops completely and the fruit reaches its maximum size; and a third period which features very little change in fruit weight and size and is characterized by several stages of fruit ripening and maturation. The ripening stages of the tomato may be broken down into mature green, breaker, turning, pink, light red and red Endogenous cytokinin concentrations are highest during the first period of fruit development and maturation and thus may be associated with the increased cell division seen in that period. It would therefore also be of interest to obtain earlier and/or increased expression of the cytokinin gene to enhance cytokinin-related effects in fruit development. Thus, of particular interest are transcriptional initiation regions which provide for tissue specificity or which are activated at a specific time in development of the plant to provide the desired level of transcription of a cytokinin gene. For example, increasing cytokinin levels at a time early in the formation of the fruit can be used to increase the number of cells in the fruit and thus the ultimate size and/or solids content of the fruit and/or mitigate the spontaneous, early abortion of fruit.

Cytokinin concentration in vivo appears to be inversely related to fruit ripening and maturation; exogenous application of cytokinins to ripening fruit can delay fruit ripening and extend shelf-life of fruit. Thus, an increase in the concentration of cytokinin in fruit in the third period of fruit ripening and maturation, when endogenous concentrations generally are low, may be expected to delay ripening.

Of particular interest is expression of cytokinins in fruit tissue especially early in fruit development. Expression as early as immediately prior to anthesis in ovary tissue or expression during the early stages of development of the fruit proper (after anthesis) is desirable. Periods of interest relating to fruit development in the growth cycle of a plant include the period at least 24 hours prior to flowering through flower senescence. The term "fruit" as used herein intends the ripened ovary wall of a flower and any other closely associated parts. (See Weirer, T.E. et al., ed., *Botany: An Introduction to Plant Biology* (6th ed.) (John Wiley & Sons, 1982); Tootill & Backmore, eds., *The Facts on a File Dictionary of Botany* (Market Home Books Ltd., 1984). The term "anthesis" as used herein intends the period associated with flower opening and flowering. Abercrombie, M., et al., *A Dictionary of Biology* (6th ed) (Penguin Books, 1973). Anthesis begins with the opening of the flower petals, which represents the beginning of a sexually receptive portion of the reproductive cycle of the plant. Typically, anthesis lasts approximately one week in the tested UCB82 tomato variety. Unopened flowers, or buds, are considered "pre-anthesis". The term "flower senescence" as used herein intends the period associated with flower death, including the loss of the flower petals, etc. Fertilization of a tomato embryo sac, to produce the zygote that will form the embryo plant, typically occurs 2-3 days after flower opening. This coincides with a decrease in the activity of an ovary tissue promoter.

To obtain expression of the cytokinin gene a host cell is transformed using an expression cassette which includes in the 5'-3' direction of transcription, a transcriptional and translational initiation region, a DNA sequence encoding an enzyme in a cytokinin metabolic pathway, and a transcriptional and translational termination region functional in plants. One or more introns may also be present. The DNA sequence may have any open reading frame encoding an enzyme involved in cytokinin metabolism, or a sequence complementary to a genomic sequence, where the sequence may be an open reading frame, an intron, a non-coding leader sequence, or any other sequence where the complementary sequence will inhibit transcription, messenger RNA processing, e.g. splicing, or translation of a cytokinin gene or enzyme involved in metabolism of a cytokinin. The DNA sequence may be synthetic, naturally derived, or combinations thereof. Depending upon the nature of the DNA sequence, it may be desirable to synthesize the sequence with plant-preferred codons. The plant preferred codons may be determined from the codons of highest frequency in the proteins expressed in the particular plant species of interest.

The cytokinin gene may be any prokaryotic or eukaryotic gene which provides for production of cytokinins (e.g. zeatin) and related cytokinin derivatives. These genes may include bacterial genes, unicellular microorganism genes, mammalian genes, or the like which encode enzymes or enzyme-intermediates that catalyze the production of the cytokinin and/or cytokinin-derivatives. The DNA sequence of interest may be prepared in a variety of ways, including synthesis, isolation from genomic DNA, preparation from cDNA, or combinations thereof from bacterial or plant sources. Of particular interest is the tmr gene or genetic locus, Akiyoshi, et al., *Proc. Nat'l Acad. Sci. USA* (1984) 81:5994-5998; Barry, et al., *Proc. Nat'l Acad. Sci. USA* (1984) 81:4776-4780, and a closely related or identical gene known in the literature as ipt (isopentenyl transferase), Smigocki, et al. (1988) supra. Other examples of cytokinin genes include the ptz gene from *Pseudomonas svringae* and the tzs locus from *A. tumefaciens*. See, for example, Powell, et al. *Nucl. Acids Res.* (1986) 14:2555-2565.

For examples of fruit specific and ovary tissue promoters, see co-pending U.S. applications Ser. No. 373,795,and Ser. No. 382,802 both filed Jul. 19, 1989,now abandoned, which disclosures are incorporated herein by reference in their entirety.

It is of interest to direct expression of the cytokinin gene to a specified tissue or tissues. Identifying useful transcriptional initiation regions may be achieved in a number of ways. Where a tissue-localized protein has been or is isolated, it may be partially sequenced, so that a probe may be designed for identifying messenger RNA specific for that tissue. As a means to enhance the concentration of the messenger RNA specifically associated with the tissue of interest, cDNA may be prepared and messenger RNA or cDNA from tissues not having the protein associated cells subtracted from it. The residual cDNA may then be used for probing the genome for complementary sequences, using an appropriate library prepared from plant cells. Alternatively, a cDNA library made from the tissue of interest is probed with labelled cDNA from the same tissue and from undesired tissues to identify cDNAs expressed in only the desired tissue. cDNA and/or sequences which hybridize to the cDNA may then be isolated, manipulated, and the 5'-untranslated region associated with the coding region isolated and used in expression constructs to identify the transcriptional activity of the 5'-untranslated region. In some instances, a probe may be employed directly for screening a genomic library and identifying sequences which hybridize to the probe. The sequences will be manipulated as described above to identify the 5'-untranslated region.

The transcriptional initiation region may be native or homologous to the host or foreign or heterologous to the host. By foreign is intended that the transcriptional initiation region is not found in the wild-type host into which the transcriptional initiation region is introduced.

Where it is desired to increase cell division in early stages of fruit development, the transcriptional initiation region should be expressed at or about anthesis; where it is desired to delay ripening, it should maintain its activity during the maturation of the green fruit, and more desirably be active through the ripening or red fruit period. Comparable periods for other fruit are referred to as stages of ripening. The invention is not limited to those transcriptional initiation regions which are activated at or shortly after anthesis but also includes transcriptional initiation regions which are activated at any of the ripening stages of the fruit.

Of particular interest are transcriptional initiation regions which provide for expression in ovary tissue, including ovary integuments (also known as "ovule epidermal cells"), core or pericarp tissue, etc. Increased levels of cytokinin in ovary tissue can effect a desired phenotypic modification using a developmentally regulated ovary-specific promoter. For example, an ovary tissue transcription initiation control region can be obtained from tomato. The promoter results in expression of abundant mRNA in ovaries prepared from unopened flowers, some mRNA in immature green fruit, no detectable hybridization in mature green fruit. Unexpectedly, the promoter shows activity in response to tomato leaf wounding. Copending U.S. application Ser. No.

382,518, filed Jul. 19, 1989, now abandoned, which disclosure is hereby incorporated by reference.

The transcription initiation control region corresponding to the cDNA clone pZ70, and sequences hybridizable to clone pZ70, i.e., clone pZ8, are of interest because of the high level of expression and tissue selectivity of clone pZ70 in ovary tissue: when pre-anthesis tomato ovaries are hybridized to sense and antisense RNA $^{35}$S-labelled probes of pZ8, the antisense constructs hybridize specifically to the inner core region of the ovary and the outer region of the ovules (the integuments). Northern analyses show hybridization to RNA isolated from ovary and fruit tissues from various stages of tomato development.

Another transcriptional initiation region of interest includes one which regulates the expression of the sequence corresponding to the tomato-derived cDNA pZ130 clone. Sequences hybridizable to the pZ130 probe, i.e. clone pZ7, show abundant messenger RNA, especially at the early stages of anthesis. The message is expressed in ovary integument and ovary outer pericarp tissue and has not been detected in other tissues or at any other stage of fruit development. Thus, the transcript initiation region is considered ovary-specific for purposes of this invention.

Also of interest for increasing cytokinin concentration in fruit is a tomato fruit-specific transcriptional initiation region, referred to as 2All, which regulates the expression of a 2All DNA sequence described in the Experimental section. The 2All transcriptional initiation region provides for abundant mRNA, being activated at or shortly after anthesis and remaining active until the red fruit stage.

Another transcriptional initiation region of interest is one which regulates expression of the enzyme polygalacturonase, an enzyme which plays an important role in fruit ripening. The polygalacturonase promoter is active in at least the breaker through red fruit stage. Other fruit-specific promoters may be activated at times subsequent to anthesis, such as prior to or during the green fruit stage, during preripe (e.g., breaker) or even into the red fruit stage.

The termination region which is employed will be primarily one of convenience, since termination regions appear to be relatively interchangeable. The termination region may be native to (from the same source as) the transcriptional initiation region, may be native to the DNA sequence of interest, or may be derived from another source, i.e., it may be heterologous and/or synthetic. Convenient termination regions are available from the Ti-plasmid of A. tumefaciens, such as the octopine synthase and nopaline synthase termination regions.

In preparing the transcription cassette, the various DNA fragments may be manipulated, so as to provide for the DNA sequences in the desired orientation, either sense or antisense, and, as appropriate, in the proper reading frame. Toward this end, adapters or linkers may be employed for joining the DNA fragments or other manipulations may be involved to provide for convenient restriction sites, removal of superfluous DNA, removal of restriction sites, or the like. Toward this end, in vitro mutagenesis, primer repair, restriction, annealing, resection, ligation, or the like may be employed, where insertions, deletions or substitutions, e.g. transitions and transversions, may be involved.

In addition to the expression cassette, depending upon the manner of introduction of the transcription construct into the plant, other DNA sequences may be required. For example, when using the Ti- or Ri-plasmid for transformation of plant cells, as described below, at least the right border and frequently both the right and left borders of the T-DNA of the Ti or Ri-plasmids will be joined as flanking regions to the transcription construct. The use of T-DNA for transformation of plant cells has received extensive study and is amply described in EPA Ser. No. 120,516, Hoekema, In: The Binary Plant Vector System Offsetdrukkerij Kanters B.V., Alblasserdam, 1985, Chapter V, Knauf et al., Genetic Analysis of Host Range Expression by Agrobacterium, In: Molecular Genetics of the Bacteria-Plant Interaction, Puhler, A. ed., Springer-Verlag, NY, 1983, p. 245, and An et al., *EMBO J.* (1985) 4:277-284.

The transcriptional construct will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced.

In carrying out the various steps, cloning is employed, so as to amplify the amount of DNA and to allow for analyzing the DNA to ensure that the operations have occurred in proper manner. A wide variety of cloning vectors are available, where the cloning vector includes a replication system functional in *E. coli* and a marker which allows for selection of the transformed cells. By appropriate manipulations, such as restriction, chewing back or filling in overhangs to provide blunt ends, ligation of linkers, or the like, complementary ends of the fragments can be provided for joining and ligation. Illustrative vectors include pBR332, pUC series, M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

A variety of techniques are available for the introduction of DNA into a plant cell host. These techniques include transformation with employing *A. tumefaciens* or *A. rhizogenes* as the transforming agent, protoplast fusion, injection, electroporation, etc. For transformation with Agrobacterium, plasmids can be prepared in *E. coli* which plasmids contain DNA homologous with the Ti-plasmid, particularly T-DNA. The plasmid may or may not be capable of replication in Agrobacterium, that is, it may or may not have a broad spectrum prokaryotic replication system, e.g., RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

As a host cell, cells from any of a number of fruit bearing plants may be employed in which the plant parts of interest are derived from the ovary wall. These include true berries such as tomato, grape, blueberry, cranberry, currant, and eggplant; stone fruits (drupes) such as cherry, plum, apricot, peach, nectarine and avocado; compound fruits (druplets) such as raspberry and blackberry. In hesperidium (oranges, citrus), the expression cassette might be expected to be expressed in the "juicy" portion of the fruit. In pepos (such as watermelon, cantaloupe, honeydew, cucumber and squash) the equivalent tissue for expression is most likely the inner edible portions, whereas in legumes (such as peas, green beans, soybeans and cotton) the equivalent tissue is the seed pod and the burr of the cotton boll, respectively.

Conveniently, explants may be cultivated with the *A. tumefaciens* or *A. rhizooenes* to allow for transfer of the transcription construct to the plant cells, the plant cells dispersed in an appropriate selective medium for selection, grown to callus, shoots grown and plantlets regenerated from the shoots by growing in rooting medium. The Agrobacterium host will contain a plasmid having the vir genes necessary for transfer of the T-DNA to the plant cells and may or may not have T-DNA. Disarmed Ti-plasmids (lacking the tumor genes, particularly those of the T-DNA region) may be introduced into the plant cell.

The cells which have been transformed may be grown into plants in accordance with conventional ways. See for example, McCormick et al., *Plant Cell Reports* (1986) 5:81–84. These plants may then be grown, and either pollinated with the same transformed strain or different strains. The resulting progeny having the desired phenotypic characteristic can then be identified. Two or more generations may be grown to ensure that the subject phenotypic characteristic is stably maintained and inherited and then seeds harvested for use to provide fruits with the new phenotypic property.

The methods and DNA constructs of the subject invention find use in modifying the characteristics of plant cells, particularly fruit cells. By transforming plant cells with a DNA construct comprising a transcriptional initiation region active at a desired stage in the development of the plant and/or in a desired tissue or tissues, cytokinin concentrations can be modulated at that desired stage and/or in that desired tissue. For example, a construct comprising a DNA sequence encoding an enzyme involved in cytokinin synthesis, such as isopentyl transferase, under the regulation of a fruit-specific promoter active during fruit ripening, where the cytokinin gene is present in the sense orientation, may be used to delay fruit ripening and/or increase shelf life of fruit. Use of a construct comprising the same DNA sequence but regulated by a promoter active at or about the time of anthesis can be used to increase cell number, which subsequently may result in an increase in fruit solids. Use of a cytokinin synthesis gene in the antisense orientation, or use of an enzyme involved in breakdown of cytokinins inserted in the construct in the sense direction under the direction of the same promoter, may be used to promote fruit maturation.

The following examples are offered by way of illustration and not by limitation.

| EXPERIMENTAL | |
|---|---|
| Table of Contents | |
| Example 1. | Construction of Tomato cDNA Banks and Screening for Clones Having Desired Specificity |
| | Screening for Fruit-Specific Clones |
| Example 2. | Screening for Ovary-Specific Clones Analysis of Fruit-Specific cDNA Clones |
| | Synthesis of RNA Probes |
| | DNA Sequencing |
| | Amino Acid Sequence |
| | Southern Hybridization |
| Example 3. | Preparation of Fruit Specific Genomic Clone Plasmids |
| | Isolation of a Genomic Clone |
| | Preparation of pCGN1273 |
| | Preparation of pCGN1267 |
| Example 4. | Analysis of Ovary-Tissue cDNA Clones |
| | Northern Analysis |
| | Expression Level |
| | Cellular Specificity |
| | Sequencing of pZ130 and pZ70 cDNA Clones |
| | Screening Genomic Library for Genomic Clones |
| | Preparation of Genomic Clones |
| Example 5. | Construction of Binary Vectors |
| | Construction of pCGN783 |
| | (a) Construction of pCGN587 |
| | (b) Construction of pCGN739 (Binary Vector) |
| | (c) Construction of pCGN726c (1 ATG-Kanamycin-3' region) |
| | (d) Construction of pCGN167 |
| | (e) Construction of pCGN766c (35S promoter-3' region) |
| | (f) Final Construction of pCGN783 |
| | Construction of pCGN1578 |
| | (a) Construction of pCGN1536 |
| | (b) Construction of pCGN1546 |
| | (c) Construction of pCGN565RB-H + X |
| | (d) Construction of pCGN1542b |
| | (e) Construction of pCGN1532 |
| | (f) Final Construction of pCGN1578 |
| Example 6. | Construction of Tagged Genomic Cassettes and Binary Vectors |
| | Isolation of Polygalacturonase Genomic Clone |
| | Sequence of Genomic Clone |
| | Preparation of pCGN1268 and pCGN1269 |
| | Preparation of pCGN1219 and pCGN1220 |
| | Preparation of pCGN1255 and pCGN1258 |
| | Preparation of pCGN1227 and pCGN1228 |
| | Preparation of pCGN1264 and pCGN1265 |
| Example 7. | Preparation of Transgenic Plants |
| Example 8. | Analysis of Tagged Genomic Constructs in Transgenic Plants |
| Example 9. | Northern Results on Transgenic Plants 2All Promoter Cassette |
| | Transcriptional Initiation Region |
| | Transcriptional and Translational Termination Region |
| | Final Construction |
| | Construction of Plasmid pCGN1241 |
| | Construction of pCGN2610 and pCGN2611 |
| Example 10. | Comparison of Different Sized 2All 5' Regions |
| | Preparation of Test Constructs |
| | Construction of pCGN2601 and pCGN2602 |
| | Construction of pCGN2812 |
| | Construction of pCGN2816 |
| | Construction of pCGN2813 and pCGN2814 (2All 5'-GUS-Tr5 3' Constructs) |
| | Analysis of GUS Enzyme Activity |
| Example 11. | 2All Constructs Comprising tmr |
| | Construction of pCGN2612 and pCGN2613 |
| | 2All-tmr Phenotypic Results |
| | Northern Analysis |
| | Cytokinin Expression |
| Example 12. | Preparation of a pZ130 Expression Construct |
| | Preparation of pCGN2901/pCGN2902 |
| | Preparation of a pZ130 Expression Construct |

-continued

EXPERIMENTAL

Table of Contents

Analysis of Transgenic Plants

Materials and Methods

Cloning Vectors

Cloning vectors used include the pUC vectors, pUC8 and pUC9 (Vieira and Messing, *Gene* (1982) 19:259-268); pUC18 and pUC19 (Norrander et al., *Gene* (1983) 26:101-106; Yanisch-Perron et al., *Gene* (1985) 33:103-119), and analogous vectors exchanging chloramphenicol resistance (CAM) as a marker for the ampicillin resistance of the pUC plasmids described above (pUC-CAM [pUC12-Cm, pUC13-Cm]Buckley, K., Ph.D. Thesis, U.C.S.D., CA 1985). The multiple cloning sites of pUC18 and pUC19 vectors were exchanged with those of pUC-CAM to create pCGN565 and pCGN566 which are CAM resistant. Also used were pUC118 and pUC119, which are respectively, pUC18 and pUC19 with the intergenic region of M13, from an HgiAI site at 5465 to the AhaIII site at 5941, inserted at the NdeI site of pUC (available from Vieira J. and Messing, J. Waksman Institute, Rutgers University, Rutgers, N.J.)

Materials

Terminal deoxynucleotide transferase (TDT), RNaseH, *E. coli* DNA polymerase, T4 kinase, and restriction enzymes were obtained from Bethesda Research Laboratories; *E. coli* DNA ligase was obtained from New England Biolabs; reverse transcriptase was obtained from Life Sciences, Inc.; isotopes were obtained from Amersham; X-gal was obtained from Bachem, Inc. Torrance, Calif.

Microbiological Deposits

The following microbiological deposits have been made with the American Type Culture Collection (ATCC), 12301 Parklawn Drive, Rockville, Md. 20852:

| Identification | Date of Deposit | Accession No. |
|---|---|---|
| pCGN1288 | July 13, 1989 | 68054 |
| pCGN783/71-18 | December 27, 1988 | 67868 |
| pCGN1299x 7118 | May 21, 1987 | 67408 |

Calgene Lambda 116 and Calgene Lambda 140, containing genomic sequence of pZ70 and pZ130, respectively, were deposited on July 13, 1989 and given ATCC Accession No. 40632 and No. 40631 respectively.

EXAMPLE 1

Construction of Tomato cDNA Banks and Screening for Clones Having Desired Specificity Tomato plants (*Lycopersicon esculentum* cv UC82B) were grown under greenhouse conditions. Poly(A)+-RNA was isolated as described by Mansson et al., *Mol. Gen. Genet.* (1985) 200:356-361. The synthesis of cDNA from poly(A)+RNA prepared from ripe fruit, cloning into the PstI site of the plasmid pUC9 and transformation into an *E. coli* vector were all as described in Mansson et al., *Mol. Gen. Genet.* (1985) supra. The synthesis of cDNA poly(A)+RNA, prepared from ovaries of unopened tomato flowers (pre-anthesis stage), was carried out using the "BRL cDNA Cloning Kit" following the manufacturer's instructions (BRL, Bethesda, Md.). Addition of restriction endonuclease EcoRI linkers (#1078, Biolabs, Beverly, Mass.) to the resulting double-stranded cDNA was done using the procedures described in Chapter 2 of DNA *Cloning Vol. 1: A Practical Approach*, Glover, D.M., ed., (IRL Press, Oxford) 1985. Cloning the cDNA into the EcoRI site of the phage Lambda ZAP (Stratagene, San Diego, Calif.) and packaging the resulting recombinant phage (using Giga-Pack Gold, Stratagene, San Diego, Calif.) was carried out as described in the respective commercial protocols.

Screening for Fruit-Specific Clones

Two thousand recombinant clones were screened by colony hybridization with radiolabeled cDNA made from tomato red fruit mRNA, whole seedling mRNA, and leaf mRNA. Bacterial colonies immobilized onto GeneScreen Plus filters (New England Nuclear), were denatured in 1.5 M NaCl in 0.5 M NaOH, then neutralized in 1.5 M NaCl in 0.5 M Tris-HCl pH 8, and allowed to air dry. Hybridization, washing and autoradiography were all performed as described in Maniatis et al., Molecular Cloning: A Laboratory Manual (1982) Cold Spring Harbor, N.Y.

Sixty-five clones were selected which had more intense hybridization signals with fruit cDNA than with leaf cDNA and therefore appeared to be under-represented in the leaf mRNA population relative to the fruit population. Replicate slot blot filters were prepared using purified DNA from the selected clones and hybridized with radioactive cDNA from leaf, green fruit, and red fruit as before. This allowed selection of cDNA clone 2AII, also referred to as pCGN1299 which is on at high levels in both the fruit stages (red and green) and off in the leaf.

Screening for Ovary-Specific Clones

Two cDNA banks were prepared as described above from the pre-anthesis stage mRNA. The first cDNA library was screened by differential hybridization using $^{32}$P-labelled cDNA probes made from pre-anthesis mRNA, leaf mRNA and immature green fruit mRNA. Clones were selected which hybridized only to the pre-anthesis mRNA. The cDNAs corresponding to the selected Lambda ZAP clones were excised from the phage vector and propagated as plasmids following the manufacturer's instructions. From an initial screen of 1000 cDNAs, two clones, clones pZ7 and pZ8, were selected for further study.

For the second library, which contained significantly longer cDNA than the first, the poly(A)+RNA sample was run through an RNA spin column, following the manufacturer's directions, prior to the cloning procedures. Several thousand recombinant clones from the second cDNA library were screened by plaque hybridization (as described in the Stratagene Cloning Kit Instruction Manual) with a mixture of radiolabeled DNA probes of interest. Screening of approximately three thousand recombinant clones from the second library with the pZ7 and pZ8 DNA probes yielded selection of fourteen clones which had intense hybridization signals. Selected clones were excised from the phage vector and propagated as plasmids. DNA was isolated from each clone, cut with the restriction endonuclease EcoRI, electrophoresed through a 0.7% agarose gel and used to conduct duplicate blot hybridizations with radiolabeled probes pZ7 and pZ8 as described in Maniatis et al., *Molecular Cloning: A Laboratory Manual* (Cold Spring Harbor, N.Y. (1982). Seven clones which hybridized to pZ7 and three cones which hybridized to pZ8 were selected. Two of the longest clones, pZ130 (pZ7-hybridizing) and pZ70 (pZ8-hybridizing) were selected for further characterization.

EXAMPLE 2

Analysis of Fruit-Specific cDNA Clones

Synthesis of RNA Probes

The cDNA insert of pCGN1299 was excised as an EcoRI to HindIII fragment of approximately 600 bp (as measured on an agarose gel), and subcloned into the Riboprobe vector pGEM1 (Promega Biotec), creating pCGN488. $^{32}$P-labeled transcripts made from each strand of the pCGN488 insert using either SP6 or T7 polymerase were used as probes in separate Northern blots containing mRNA from leaf, immature green and mature red fruits. The RNA transcript from the SP6 promoter did not hybridize to the tomato mRNA. However, the transcript from the T7 promoter hybridized to an mRNA of approximately 700 nt in length from the green fruit and the red fruit but not to mRNA from tomato leaf. The direction of transcription of the corresponding mRNA was thus determined.

The tissue specificity of the pCGN1299 cDNA was demonstrated as follows. RNA from root, stem, leaf, and seven stages of fruit development (immature green, mature green, breaker, turning, pink, light red, and red) was sized on formaldehyde/agarose gels according to the method described by Maniatis et al., (1982), supra, immobilized on nitrocellulose and hybridized to $^{32}$P-labeled RNA which was synthesized in vitro from pCGN488 using T7 polymerase. Each lane contained 100 ng of polyA+RNA except for two lanes (pink and light red lanes) which contained 10 μg of total RNA. The Northern analysis of mRNA from root, stem, leaf, and fruit at various stages of fruit development indicated that pCGN1299 cDNA was expressed in all stages of fruit development from the early stages immediately after anthesis to red ripe fruit. No mRNA hybridizing to pCGN1299 was found in leaf, stem, or root tissue. The size of the mRNA species hybridizing to the pCGN488 probe was approximately 700 nt.

Message abundance corresponding to the pCGN1299 cDNA was determined by comparing the hybridization intensity of a known amount of RNA synthesized in vitro from pCGN488 using SP6 polymerase to mRNA from red tomato fruit in a Northern blot. The $^{32}$P-labeled transcript from pCGN488 synthesized in vitro using T7 polymerase was used as a probe. The Northern analysis was compared to standards which indicated that the pCGN1299 cDNA represents an abundant mRNA class in tomato fruit, being approximately 1% of the message.

DNA Sequencing

The polyA+sequence was missing from pCGN1299 cDNA. A longer cDNA clone, pCGN1298, therefore was identified by its hybridization with the pCGN488 probe. The complete DNA sequence of the two cDNA inserts was determined using both Maxam-Gilbert and the Sanger dideoxy techniques and is as follows. The sequence of pCGN1298 contains additional sequences at both the 5' and 3' end compared to pCGN1299. The sequences are identical over the region that the two clones have in common.

Amino Acid Sequence

The pCGN1299 cDNA sequence was translated in three frames. The longest open reading frame starts from the first ATG. Both pCGN1299 and pCGN1298 have an open reading frame which encodes a 96 amino acid polypeptide. The protein has a hydrophobic N-terminus which may indicate a leader peptide for protein targeting. A hydrophobicity profile was calculated using the Hoop and Woods, (*Proc. Natl. Acas. Sci. USA* (1981) 78:3824-3828) algorithm. Residues 10-23 have an extremely hydrophobic region.

Southern Hybridization

Southern analysis was performed as described by Maniatis et al. (1982), supra. Total tomato DNA from cultivar UC82B was digested with EcoRI or HindIII, separated by agarose gel electrophoresis and transferred to nitrocellulose. Southern hybridization was performed using a $^{32}$P-labeled probe produced by nick translation of pCGN488 (Maniatis et al., (1982) supra). The simple hybridization pattern indicated that the gene encoding pCGN1299 cDNA was present only in a few copies or perhaps even one only copy in the tomato genome.

EXAMPLE 3

Preparation of Fruit-Specific

Genomic Clone Plasmids

Two genomic clone plasmids were prepared, pCGN1273 and pCGN1267. They were obtained as follows.

Isolation of a Genomic Clone

A genomic library established in Charon35/Sau3A constructed from DNA of the tomato cultivar VFNT-Cherry was screened using the [$^{32}$P]-RNA from cDNA clone PCGN488 as a probe. A genomic clone containing approximately 12.5 kb of sequence from the tomato genome was isolated. The region which hybridizes to a pCGN488 probe spans an XbaI restriction site which was found in the cDNA sequence and includes the transcriptional initiation region designated 2All.

Preparation of pCGN1273

The region surrounding the XbaI restriction site, approximately 2.4 kb in the 5' direction and approximately 2.1 kb in the 3' direction was subcloned to provide an expression cassette. The 5' XhoI to XbaI fragment and the 3' XbaI to EcoRI fragment from the 211 genomic clone were inserted into a pUC-derived chloramphenicol plasmid containing a unique XhoI site and no XbaI site. This promoter cassette plasmid is called pCGN1273. The complete sequence of the 2All genomic DNA cloned into pCGN1273 from the XhoI site (position 1 at the 5' end) to the EcoRI site (position 4654) was determined by Sanger dideoxy techniques. The sequence of the genomic clone is identical to the pCGN1299 cDNA clone over the region they have in common as is shown in FIG. 4 of co-pending U.S. application No. 382,176 filed Jul. 19, 1989, now abandoned. The sequence reported previously (see USSN 188,361 filed Apr. 29, 1988, now abandoned,) corresponds to position 1169 to 2645 of the complete sequence.

Preparation of pCGN1267 pCGN1267 was constructed by deleting from pGN1273 a portion of the plasmid polylinker from the EcoRV site to the BamHI site. Two DNA sequences were inserted into pCGN1273 at the unique XbaI site (position 2494). This site is in the 3' non-coding region of the 2All genomic clone before the poly A site.

EXAMPLE 4

Analysis of Ovary-Tissue cDNA Clones

Northern Analysis

Tissue specificity of the cDNA probe was demonstrated as follows: RNA was isolated from 1, 2, 3, 4, 5, 6, 7, 10, 14, 17 and 21 days post-anthesis, anthesis and pre-anthesis stage tomato ovaries, tomato leaves and unorganized tomato callus using the method of Ecker et al. (*Proc. Natl. Acad. Sci. USA* (1987) 84:5203) with the following modifications. After the first precipitation of the nucleic acid, the pellets are resuspended in 2 ml of diethylpyrocarbonate (DEP)-treated water at 4° C. The solutions were brought to 1 mM $MgCl_2$ and $\frac{1}{4}$ volume of 8 M LiCl was added. The samples were mixed well and stored at 4° C overnight. The samples are then centrifugated at 8,000 RPM for 20 min. at 4° C. The pellets are dried, resuspended in DEP-treated water on ice and ethanol-precipitated. The RNA's were electrophoresed on formaldehyde/agarose gels (according to the method of Fourney et al. Focus (1988) 10:5–7), immobilized on Nytran membranes (Schleicher and Schuel) and hybridized to $^{32}$P-labeled probes.

From Northern analysis, pZ7 and the pZ8 genes are most highly expressed at anthesis in UC82B, less highly expressed prior to and the day after the opening of the flower. By two days after the onset of anthesis, expression of both genes had decreased significantly. From two days post-anthesis, pZ8 RNA expression continued at a relatively low level and was apparently constitutive. pZ7 RNA accumulation continued to decrease until by three weeks postanthesis it was undetectable. No RNA hybridizing to pZ7 or pZ8 was found in callus tissue. No RNA hybridizing to pZ7 was found in leaf tissue. A barely detectable hybridization signal for pZ8 was seen with leaf RNA. The size of the mRNA species hybridizing to the pZ7 probe was about 800 nt and to the pZ8 probe about 500 nt.

Expression Level

Message abundance corresponding to the cDNA probes was determined by comparing the hybridization intensity of a known amount of RNA synthesized in vitro from the clones using T7 RNA polymerase in the Riboprobe System to RNA from anthesis stage and three week old tomato ovaries. Based upon this analysis, pZ7 and pZ8 cDNAs represent abundant RNA classes in anthesis-stage tomato ovaries, being approximately 5% and 2% of the message, respectively.

Cellular Specificity

The cellular specificity of the cDNA probes was demonstrated using in situ hybridization. Pre-anthesis stage UC82B tomato ovaries were fixed in 4% paraformaldehyde/ phosphate buffered saline (PBS), 5 mM $MgCl_2$ solution, pH 7.4. Tissue was fixed overnight then passed through a graded tertiary butyl alcohol (TBA) series starting at 50% alcohol, then, infiltrated the Paraplast and cast into paraffin blocks for sectioning (Berlyn and Miksche, *Botanical Microtechnique and Cytochemistry*, (1976) Iowa). Embedded ovaries were transversely cut, 8 μm thick, on a Reichert Histostat rotary microtome. Paraffin ribbons holding 5–7 ovary sections were affixed to gelatin-chrom alum subbed slides (Berlyn and Miksche (1976) supra) and held in a dust-free box until in situ hybridizations were performed. Slides were then deparaffinized in xylene and rehydrated by passing through an ethanol hydration series (Singer et al., *Biotechniques* (1986) 4:230–250).

A 2X hybridization mix was made consisting of 100 μl 20X SSC, 20 μl 10% BSA, 100 μl 750 mM DTT, 200 μl 50% dextran sulfate, 50 μl RNasin, and 30 μl sterile water. Sense and antisense $^{35}$S-RNA probes were generated from the cDNAs of interest using T3 and T7 RNA polymerases in in vitro transcription reactions following the manufacturer's protocol (Riboprobe). 2.5 μl, tRNA (20 mg/ml), 2.5 μl salmon sperm DNA (10 mg/ml) $4 \times 10^6$ cpm probe were dried down then resuspended in 25 μl 90% formamide and 25 μl 1 2X hybridization mix per slide. Forty μl of this hybridization mix was placed on each slide. A cover slip was placed over the sections and the edges sealed. Slides were placed in a 37° C. dry oven overnight to hybridize. Posthybridization treatments were as described in Singer et al., 1986), supra. Autoradiography was performed as described in Kodak Materials for Light Microscope (1986, available from Kodak, Rochester, N.Y.) using Kodak liquid emulsion NTB-3. Slides were exposed for approximately two weeks. Sections were stained in 0.05% toluidine blue and then dehydrated by incubation for five minutes each in a graded alcohol series: xylene:100% ethanol, 1:1, followed by 2 changes of 100% xylene. Coverslips were mounted with cytoseal and the slides dried (45–50° C., 1–2 days).

When pre-anthesis tomato ovaries were hybridized to sense and antisense $^{35}$S-pZ7 RNA, the antisense transcripts hybridized specifically to the outer pericarp region of the ovary and to the outer region of the ovules (the integuments). The sense transcripts (negative control) showed no hybridization. When pre-anthesis tomato ovaries were hybridized to sense and antisense $^{35}$S-pZ8 RNA, the antisense transcripts hybridized specifically to the inner core region of the ovary and to the outer region of the ovules (the integuments). The sense transcripts (negative control) showed no hybridization.

From the above, it is seen that the mRNA transcripts encoded by the genes corresponding to pZ7 and pZ8 are abundantly expressed during a very specific stage of tomato fruit development and appear to be expressed in a specific subset of tomato ovary cell types during that stage.

Sequencing of pZ130 and pZ70 cDNA Clones

The DNA sequences of pZ130 and pZ70 were determined by using the Sanger et al. (1971) dideoxy technique. The DNA sequences of both pZ130 and pZ70 were translated in three frames. The sequence, including the longest open reading frame, for each is given in FIGS. 1 and 4, respectively, of co-pending U.S. application No. 382,518 filed Jul. 19, 1989.

Screening Genomic Library for Genomic Clones

Southern analysis was performed as described by Maniatis et al., (1982) supra. Total tomato DNA from cultivar UC82B was digested with the restriction endonucleases EcoRI, HindIII and BamHI, separated by agarose gel electrophoresis and transferred to nitrocellulose. Southern hybridizations were performed using $^{32}$P-labelled probes produced by nick translation or by random priming of pZ130 or pZ70. Simple hybridization patterns were observed with all cDNA clones (pZ7 and pZ130 patterns were identical to each other and pZ8 and pZ70 patterns were identical to each other) indicating that single, or perhaps two, genes encode the respective messages in the tomato genome. Additional analysis using a pZ130 hybridization probe to hybridize to tomato genomic DNA digested with the restriction endonuclease BglII indicated that this gene was actually a member of a small (approximately 5-7 member) family of genes. The original pZ7 cDNA clone, however, hybridized specifically to one or perhaps two bands using BglII digested tomato genomic DNA.

Preparation of Genomic Clones

Two genomic clones, one representing each cDNA clone pZ130 and pZ70, were obtained as follows. A genomic library constructed from DNA of the tomato cultivar UC82B partially digested with the restriction endonuclease Sau3A was established in the lambda phage vector, lambda-FIX according to the manufacturer's instructions (Stratagene, La Jolla, Calif.). This library was screened using $^{32}$P-labelled pZ130 or pZ70 as a probe. A genomic clone containing approximately 14.5 kb of sequence from the tomato genome and hybridizing to pZ70 was isolated. The region which hybridizes to the pZ70 probe is found within the approximately 2 kb XbaI-HindIII restriction fragment of Calgene Lambda 116. Another genomic clone containing approximately 13 kb of sequence from the tomato genome and hybridizing to pZ130 (and pZ7) is isolated. The region which hybridizes to the pZ130 probe is found within the larger EcoRI-HindIII restriction fragment of Calgene Lambda 140.

EXAMPLE 5

Construction of Binary Vectors

Construction of pCGN873 pCGN783 is a binary plasmid containing the left and right T-DNA borders of *A. tumefaciens* octopine Ti-plasmid pTiA6 (Currier and Nester, *J. Bacteriol.* (1976) 126:157-165) the gentamicin resistance gene of pPHlJl (Hirsch et al., Plasmid (1984) 12:139-141), the 35S promoter of cauliflower mosaic virus (CaMV) (Gardner et al., *Nucleic Acid Res.* (1981) 9:1871-1880); the kanamycin resistance gene of Tn5 (Jorgensen, *Mol. Gen.* (1979) 177:65); and the 3' region from transcript 7 of pTiA6 (Currier and Nester, supra (1976)).

(a) Construction of pCGN587

The HindIII-SmaI fragment of Tn5 containing the entire structural gene for APH3'II (Jorgensen et al., *Mol. Gen.* (1979) 177:65), was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment, pCGN300, containing the 3' portion of the APH3'II gene, was then combined with an EcoRI-8amHI-SalI-PstI linker into the EcoRI site of pUC7 pCGN546W). Since this construct does not confer kanamycin resistance, kanamycin resistance was obtained by inserting the BglI-PstI fragment of the APH3'II gene into the BamHI-PstI site (pCGN546X). This procedure reassembles the APH3'II gene, so that EcoRI sites flank the APH3'II gene. An ATG codon was upstream from and out of reading frame with the ATG initiation codon of APH3'II. The undesired ATG was avoided by inserting a Sau3A-PstI fragment from the 5' end of APH3'II, which fragment lacks the superfluous ATG, into the BamHI-PstI site of pCGN546W to provide plasmid pCGN550. The EcoRI fragment of pCGN550 containing the APH3'II gene was then cloned into the EcoRI site of pUC8-pUC13 (K. Buckley supra (1985)) to give pCGN551.

Each of the EcoRI fragments containing the APH-3'II gene was then cloned into the unique EcoRI site of pCGN451, which contains an octopine synthase cassette for expression to provide pCGN548 (2ATG)) and pCGN552 (1ATG). The plasmid pCGN451 having the ocs 5' and the ocs 3' in the proper orientation was digested with EcoRI and the EcoRI fragment from pCGN551 continuing the intact kanamycin resistance gene inserted with EcoRI site to provide pCGN552 having the kanamycin resistance gene in the proper orientation. This ocs/KAN gene was used to provide a selectable marker for the trans type binary vector pCGN587.

The 5' portion of the engineered octopine synthase promoter cassette consists of pTiA6 DNA from the XhoI at bp 15208-13644 (Barker et al., supra (1983)), which also contains the T-DNA boundary sequence (border) implicated in T-DNA transfer. In the plasmid pCGN587, the osc/KAN gene from pCGN552 provides a selectable marker as well as the right border. The left boundary region was first cloned in M13mp9 as a HindIII-SmaI piece (pCGN502) (base pairs 602-2212) and recloned as a KpnI-FcoRI fragment in pCGN565 to provide pCGN580. pCGN565 is a cloning vector based on pUC8-Cm, but containing pUC18 linkers. pCGN580 was linearized with BamHI and used to replace the smaller BglI fragment of pVCK102 (Knauf and Nester, Plasmid (1982) 8:45), creating pCGN585. By replacing the smaller SalI fragment of pCGN585 with the XhoI fragment from pCGN552 containing the ocs/KAN gene, pCGN587 was obtained.

(b) Construction of pCGN739 (Binary Vector)

To obtain the gentamicin resistance marker, the resistance gene was isolated from a 3.1 kb EcoRI-PstI fragment of pPHIJI (Hirsch et al., *Plasmid* (1984) 12:139-141) and cloned into pUC9 (Vieira et al., *Gene* (1982) 19:259-268) yielding pCGN549. The pCGN549 HindIII-BamHI fragment containing the gentamicin resistance gene replaced the HindIII-BglII fragment of pCGN587 creating pCGN594.

The pCGN594 HindIII-8amHI region which contains an ocs-kanamycin-ocs fragment was replaced with the HindIII-BamHI polylinker region from pUC18 (Yanisch-Perron, *Gene* (1985) 33:103-119) to make pCGN739.

(c) Construction of 726c (1 ATG-Kanamycin-3' region)

pCGN566 contains the EcoRI-HindIII linker of pUC18 (Yanisch-Perron, ibid) inserted into the EcoRI-HindIII sites of pUC13-Cm (K. Buckley (1985) supra). The HindIII-BglII fragment of pNW31c-8, 29-1 (Thomashow et al., Cell (1980) 19:729) containing ORF1 and 2 (Barker et al., Plant *Mol. Biol.* (1984) 2:335-350) was subcloned into the HindIII-BamHI sites of pCGN566 producing pCGN703.

The Sau3A fragment of pCGN703 containing the 3' region of transcript 7 from pTiA6 (corresponding to bases 2396-2920 of pTi15955 (Barker et al., supra (1984))

was subcloned into the BamHI site of pUC18 (Yanisch-Perron et al., supra (1985)) producing pCGN709.

The EcoRI-SmaI polylinker region of pCGN709 was replaced with the EcoRI-SmaI fragment from pCGN587 (see Example 5(a) above) which contains the kanamycin resistance gene (APH3'II) producing pCGN726.

The EcoRI-SalI fragment of pCGN726 plus the BglII-EcoRI fragment of pCGN734 were inserted into the BamHI-SalI sites of pUC8-pUC13-cm (Buckley (1985), supra) producing pCGN738. To construct pCGN734, the HindIII-SphI site of M13mp19 (Norrander et al., Gene (1983) 26:101-106). Using an oligonucleotide corresponding to bases 3287 to 3300, DNA synthesis was primed from this template. Following S1 nuclease treatment and HindIII digestion, the resulting fragment was cloned into the HindIII-SmaI site of pUC19 (Yanisch-Perron et al., supra (1985)). The resulting EcoRI to HindIII fragment of pTiA6 (corresponding to bases 3390-4494) was inserted into the EcoRI site of pUC8 (Vieira and Messing, supra (1982)) resulting in pCGN734. pCGN726c is derived from pCGN738 by deleting the 900 bp EcoRI-EcoRI fragment.

(d) Construction of pCGN167 pCGN167 is a construct containing a full clength CaMV promoter, 1 ATG-kanamycin gene, 3' end and the bacterial Tn903-type kanamycin gene. MI is an EcoRI fragment from pCGN550 (see construction of pCGN587) and was cloned into the EcoRI cloning site in the 1 ATG-kanamycin gene proximal to the polylinker region of M13mp9. See copending application Ser. No. 920,574, filed Oct. 17, 1986, now abandoned, which disclosure is incorporated herein by reference.

To construct pCGN167, the AluI fragment of CaMV (bp 7144-7735) (Gardner et al., Nucl. Acids Res. (1981) 9:2871-2888) was obtained by digestion with AluI and cloned into the HindII site of M13mp7 (Vieira, Gene (1982) 19:259) to create C614. An EcoRI digest of C614 produced the EcoRI fragment from C614 containing the 35S promoter which was cloned into the EcoRI site of pUC8 (Vieira et al., Gene (1982) 19:259) to produce pCGN146. To trim the promoter region, the BglII site (bp 7670) was treated with BglII and Bal31 and subsequently a BglII linker was attached to the Bal31 treated DNA to produce pCGN147.

pCGN148a containing the promoter region, selectable marker (KAN with 2 ATGs) and 3' region was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528. pCGN528 was made as follows. pCGN525 was made by digesting a plasmid containing Tn5 which harbors a kanamycin gene (Jorgenson et al., Mol. Gen. (1979) 177:65) with HindIII-BamHI and inserting the HindIII-BamHI fragment containing the kanamycin gene into the HindIII-BamHI sites in the tetracycline gene of pACYC184 (Chang and Cohen, J. Bacteriol. (1978) 134:1141-1156). pCGN526 was made by inserting the BamHI fragment 19 of pTiA6 (Thomashow et al., Cell (1980) 19:729-739) into the BamHI site of pCGN525. pCGN528 was obtained by deleting the small XhoI fragment from pCGN526 by digesting with XhoI and religating.

pCGN149a was made by cloning the BamHI kanamycin gene fragment from pMB9KanXXI into the BamHI site of pCGN148a. pMB9KanXXI is a pUC4K variant (Vieira and Messing, Gene (1982) 19:259-268) which has the XhoI site missing but contains a functional kanamycin gene from Tn903 to allow for efficient selection in Agrobacterium. pCGN149a was digested with BglII and SPhI. This small BglII-SphI fragment of pCGN149a was replaced with the BamHI-SphI fragment from MI (see below) isolated by digestion with BamHI and SphI. This produces pCGN167.

Construction of pCGN766c (35S promoter-3' region)

The HindIII-BamHI fragment of pCGN167 containing the CaMV-35S promoter, 1 ATG-kanamycin gene and the BamHI fragment 19 of pTiA6 was cloned into the BamHI-HindIII sites of pUC19 (Norrander et al., supra (1985); Yanisch-Perron et al., supra (1985)) creating pCGN976.

The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3' for construction see supra) into the HindIII-SalI sites of pCGN566 creating pCGN766c.

(f) Final Construction of pCGN783

The 0.7 kb HindIII-EcoRI fragment of pCGN766c (CaMV-35S promoter) was ligated to the 1.5 kb EcoRI-SalI fragment of pCGN726c (1-ATG-KAN-3' region) into the HindIII-SalI sites of pUC119 (J. Vieira, Rutgers University, New Jersey) to produce pCGN778. The 2.2 kb region of pCGN778, a HindII-SalI fragment containing the CaMV 35S promoter (1-ATG-KAN-3' region), replaced the HindIII-SalI polylinker region of pCGN739 to produce pCGN783.

A DNA construct comprising a DNA sequence of interest may be inserted into the binary plasmid containing a plant kanamycin resistance marker, between the left and right borders. The resulting plasmid binary vector in a host microorganism such as E. coli C2110 is conjugated into A. tumefaciens containing a disarmed Ti-plasmid capable of transferring the DNA sequence of interest and the kanamycin resistance cassette into the plant host genome. The Agrobacterium system which is employed is A. tumefaciens PC2760 (G. Ooms et al., Plasmid (1982) 7:15-29; Hoekema et al., Nature (1983) 303:179-181; European patent application No. 84-200239.6, 2424183) which disclosures are incorporated herein by reference.

Construction of pCGN1578 pCGN1578 is a binary plant transformation vector containing the left and right T-DNA borders of Agrobacterium tumefaciens octopine Ti-plasmid pTiA6 (Currier and Nester, J. Bact. (1976) 126 157-165), the gentamicin resistance gene of pPH1J1 (Hirsch and Beringer, Plasmid (1984) 12:139-141), an Agrobacterium rhizogenes Ri plasmid origin of replication from pLJbBll (jouanin et al., Mol. Gen. Genet. (1985) 201:370-374), a 35S promoter-Kan$^R$-tml$^3$ region capable of conferring kanamycin resistance to transformed plants, a ColEl origin of replication from pBR322 (Bolivar et al., Gene (1977) 2:95-113), and a lacZ' screenable marker gene from pUC18 (Yanish-Perron et al., Gene (1985) 53:103-119).

(a) Construction of pCGN1536

A 5.4 kb EcoRI fragment was removed from pV232 (Knauf and Nester, Plasmid (1982) 8:45), by EcoRI digestion and cloned into EcoRI digested pACYC184 (Chang and Cohen, J. Bacteriol. (1978) 134:1141-1156)

to create pCGN14. The 1434 bp ClaI-SPhI fragment of pCGN14, containing the mas 5' region (bp20128-21562 according to numbering of (Barker et al., *Plant Mol. Biol.* (1983) 2:335-350) was cloned into AccI-SphI digested pUC19 (Yanisch-Perron et al., *Gene* (1985) 53:103-119) to generate pCGN40. A 746 bp EcoRV-NaeI fragment of the mas 5' region was replaced by an XhoI site by digesting pCGN40 with EcoRV and NaeI followed by ligation in the presence of synthetic XhoI linker DNA to create pCGN1036. The 765 bp SstI-HindIII fragment (bp 18474-19239) of pCGN14, containing the mas 3' region, was cloned into SstI-HindIII digested pUC18 (Norrander et al., *Gene* (1983) 26:101-106) to yield pCGN43. The HindIII site of pCGN43 was replaced with an EcoRI site by digestion with HindIII, blunt ending with Klenow enzyme, and ligation with synthetic EcoRI linker DNA to create pCGN1034. The 767 bp EcoRI fragment of pCGN1034 was cloned into EcoRI-digested pCGN1036 in the orientation that places bp 19239 of the mas 3' region proximal to the mas 5' region to create pCGN1040. pCGN1040 was subjected to partial digestion with SstI, treated with T4 DNA polymerase to create blunt ends, and ligated in the presence of synthetic XhoI linker DNA. A clone was selected in which only the SstI site at the junction of bp 18,474 (mas DNA) and the vector DNA was replaced by an XhoI site to generate pCGN1047.

pCGN565 (a cloning vector based upon pUC8-cm bt containing pUC18 linkers) was digested with EcoRI and HindIII, treated with Klenow enzyme to create blunt ends, and ligated in the presence of synthetic XhoI linker DNA to create pCGN1003; this recreated the EcoRI site adjacent to the XhoI linker. pCGN1003 was digested with EcoRI, treated with Klenow enzyme to create blunt ends, and ligated in the presence of synthetic PstI linker DNA to create pCGN1007. The 1.5 kb XhoI fragment of pCGN1047, containing the mas 5' region and the mas 3' region with a multiple cloning site between, was cloned into XhoI digested pCGN1007 to construct pCGN1052. A portion of the multiple cloning site of pCGN1052 was deleted by digestion with XbaI and SstI, treated with Klenow enzyme to make blunt ends, and ligated to generate pCGN1052ΔXS.

To prepare pCGN50, the HindIII-SmaI fragment of Tn5 containing the entire structural gene for APHII (Jorgensen, et al., *Mol. Gen. Genet.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment of pCGN300, containing the 3' portion of the APHII gene, was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5' end of APHII, which fragment lacks the superfluous ATG, into the BamHI-PstI site of pCGN546W to provide plasmid pCGN550.

The 1 kb EcoRI-SmaI fragment of pCGN550 containing the 1 ATG-kanamycin resistance gene, was cloned into EcoRI-SmaI digested to create pBSKm; this plasmid contained an M13 region allowing generation of single stranded DNA. Single stranded DNA was generated according to the supplier's recommendations, and in vitro mutagenesis was performed (Adelman et al., *DNA* (1983) 2:183-193) using a synthetic oligonucleotide with the sequence 5'GAACTCCAGGAC-GAGGC3' to alter a PstI site within the kanamycin resistance gene, creating pCGN1534. pCGN1534 was digested with SmaI and ligated in the presence of a synthetic EcoRI linker DNA to generate pCGN1535. The 1 kb EcoRI fragment of pCGN1535 was cloned into EcoRI digested pCGN1052ΔXS to create the mas 5'-kan-mas 3' plant selectable marker cassette pCGN1536.

(b) Construction of pCGN1546 pCGN149a (see above) was digested with HindIII and BamHI and ligated to pUC8 digested with HindIII and BamHI to produce pCGN169 This removed the Tn903 kanamycin marker. pCGN565 (a cloning vector based on pUC8-Cm but containing pUC18 linkers) and pCGN169 were both digested with HindIII and PstI and ligated to form pCGN203, a plasmid containing the CaMV 35S promoter and part of the 5'-end of the Tn5 kanamycin gene (up to the PtI site, (Jorgenson et al., (1979), supra)). A 3'regulatory region was added to pCGN203 from pCGN204. pCGN204 was made by cloning the EcoRI fragment of CaMV (p 408-6105) containing the region V 3' region into pUC18 (Gardner, et al. (1981) supra). pCGN203 and pCGN204 were digested with HindIII and PstI and the 3' regulatory region of pCGN204 was inserted into pCGN203. The resulting cassette, pCGN206, was digested with HindIII. The ends were filled-in with Klenow polymerase and XhoI linkers were added. The resulting plasmid was called pCGN986X. pBRX25 (construction of this plasmid is described in European application EPA 0 229 042 filed Jan. 7, 1987, which application is incorporated herein by reference) contains only 11 bp of the 5' untruncated region of the nitrilase gene. The BamHI-SacI fragment of pBRX25 was inserted into BamHI-SacI digested pCGN986X yielding pBRX66. pBRX66 was digested with PstI and EcoRI, blunt ends generated by treatment with Klenow polymerase, and XhoI linkers added. The resulting plasmid, pBRX68, had a tml 3' region of approximately 1.1 kb. pBRX68 was digested with SalI and SacI, blunt ends generated by treatment with Klenow polymerase, and EcoRI linkers added. The resulting plasmid, pCGN986XE, is a 35S promoter-tml 3' expression cassette lacking the nitrilase gene. The Tn5 kanamycin resistance gene was then inserted into pCGN986XE. The 1.0 kb EcoRI fragment of pCGN1536 was ligated into pCGN986XE digested with EcoRI. A clone with the Tn5 kanamycin resistance gene in the correct orientation for transcription and translation was chosen and called pCGN1537b. The 35S promoter Kan$^R$-tml 3' region was then transferred to a chloramphenicol resistant plasmid backbone, pCGN786. pCGN786 is a pUCCM based vector with the synthetic oligonucleotide 5'GGAATTCGT-CGACAGATCTCTGCAGCTCGAGGGATC-CAAGCTT 3' containing the cloning sites EcoRI, SalI, BglII, PstI XhoI, BamHI, and HindIII inserted into pCGN566. pCGN566 contains the EcoRI-HindIII linker of pUC18 inserted into the EcoRI-HindIII sites of pUC13-Cm. pCGN786 was digested with XhoI and the XhoI fragment of pCGN1537b containing the 35S promoter-Kan$^R$-tml 3' region was ligated in. The resulting clone was termed pCGN1546.

(c) Construction of pCGN565RB-H+X pCGN451, which includes an octopine cassette containing about 1556 bp of the 5' non-coding region of the octopine synthase gene fused via an EcoRI linker to the 3' non-coding region of the octopine synthase gene of pTiA6, was digested with HpaI and ligated in the presence of synthetic SphI linker DNA to generate pCGN55. The pTi coordinates are 11,207 to 12,823 for the 3' region, and 13,643 to 15,208 for the 5' region as defined by Barker et al., *Plant Mol. Biol.* 1983) 2:325. The XhoI-SphI fragment of pCGN55 (bp 13,800 15,208, including the right border of *Agrobacterium tumefaciens* T-DNA; (Barker et al., *Gene* (1977) 2:95 113) was cloned into SalI-SphI digested of pUC19 (Yanisch-Perron et al., *Gene* (1985) 53:103–119) to create pCGN60. The 1.4 kb HindIII-BamHI fragment of pCGN60 was cloned into HindIII-BamHI digested pSP64 (Promega, Inc.) to generate pCGN1039. pCGN1039 was digested with SmaI and NruI (deleting bp 14,273–15,208; (Barker et al., *Gene* 1977) 2:95–113) and ligated in the presence of synthetic BglII linker DNA creating pCGN1039NS. The 0.47 kb EcoRI-HindIII fragment of pCGN1039NS was cloned into EcoRI-HindIII digested pCGN565 to create pCGN565RB. pCGN565 is a cloning vector based on pUC8-Cm, but containing pUC18 linkers. The HindIII site of pCGN565RB was replaced with an XhoI site by HindIII digestion, treatment with Klenow enzyme, and ligation in the presence of synthetic XhoI linker DNA to create pCGN565RB-H+X.

(d) Construction of pCGN1542b pCGN65 was constructed as follows. First, pCGN501 was constructed by cloning a 1.85 kb EcoRI-XhoI fragment of pTiA6 (currier and Nester, *J. Bact.* (1976) 126:157–165) containing bases 13,362–15,208 (Barker, et al., *Plant Molec. Biol.* (1983) 2:335–350) of the T-DNA (right border), into EcoRI-SalI digested M13mp9 (Vieira and Messing, *Gene* (1982) 19:259–268).

502 was constructed by cloning a 1.6 kb HindIII-SmaI fragment of pTiA6, containing bases of 602–2,212 of the T-DNA (left border), into HindIII-SmaI digested M13mp9. pCGN501 and pCGN502 were both digested with EcoRI and HindIII and both T-DNA-containing fragments cloned together into HindIII digested pUC9 (Vieira and Messing, *Gene* (1982) 19:259–268) to yield pCGN503, containing both T-DNA border fragments. pCGN503 was digested with HindIII and EcoRI and the two resulting HindIII-EcoRI fragments (containing the T-DNA borders) were cloned into EcoRI digested pC79 (Hohn and Collins, *Gene* (1980) 11:291–298) to generate pCGN518. The KpnI-EcoRI fragment from pCGN518, containing the left T-DNA border, was cloned into KpnI-EcoRI digested pCGN565 to generate pCGN580. The BamHI-BglII fragment of pCGN580 was cloned into the BamHI site of pACYC184 (Chang and Cohen, *J. Bacteriol.* (1978) 134:1141–1156) to create pCGN51. The 1.4 kb BamHI-SphI fragment of pCGN60 containing the T-DNA right border fragment, was cloned into BamHI-SphI digested pCGN51 to create pCGN65. To make pCGN65KX-S+X, pCGN65 was digested with KpnI and XbaI, treated with Klenow enzyme to create blunt ends, and ligated in the presence of synthetic BglII linker DNA.

pUC18 was digested with HaeII to release the lacZ' fragment, treated with Klenow enzyme to create blunt ends, and the lacZ- containing fragment ligated into pCGN565RB-H+X, which had been digested with AccI and SphI and treated with Klenow enzyme, resulting in pCGN565RBα3X. In pCGN565RBα3X, the lac promoter is distal to the right border. Both clones are positive for lacZ' expression when plated on an appropriate host. Each contain bp 13990-142773 of the right border fragment (Barker et al. (1983) supra), the AccI-SphI fragment (bp 13800-13990) having been deleted. The 728 bp BglHI-XhoI fragment of pCGN565RB3X, containing the T-DNA right border piece and the lacZ' gene, were cloned into BglII-XhoI digested pCGN65ΔKX-S+X, replacing the BglII-XhoI right border fragment of pCGN650ΔKX-S+H, to create pCGN653αX.

The ClaI fragment from pCGN653αX was deleted and replaced with an XhoI linker by digesting with ClaI, treating with Klenow enzyme to create blunt ends, and ligating in the presence of synthetic XhoI linker DNA to create pCGN65α3XX. pCGN65α3XX was digested with BglII and EcoRV, treated with Klenow polymerase, and BglII linkers added. The resulting plasmid, pCGN65α3XX', now lacks an approximately 20 bp piece of DNA that was present in pCGN65α3XX.

pBR322 (Boliver et al., *Gene* (1977) 2:95–113) was digested with EcoRI and PvuII, treated with Klenow polymerase to generate blunt ends, and BglII linkers added. An ampicillin resistant, tetracycline sensitive clone, pCGN1538 was selected. This clone now lacks the approximately 2.2 kb EcoRI-PvuII fragment containing the tetracycline resistance gene. The PvuII site has been lost but the EcoRI site was regenerated upon addition of BglII linkers.

pCGN65α3XX, was digested with BglII and ligated to BglII digested pCGN1538 to create pCGN1542a which contained both plasmid backbones. pCGN1542a was digested with XhoI and religated. An ampicillin resistant, chloramphenicol sensitive clone was chosen which lacked the pACYC184 backbone, creating pCGN1542b.

(e) Construction of pCGN1532

The EcoRI-PstI fragment containing the gentamicin resistance gene was removed from pPhlJI (Hirsch and Beringer, Plasmid (1984) 12:139–141) by EcoRI-PstI digestion and cloned into EcoRI-PstI digested pUC9 (Vieira and Messing. *Gene* (1982) 19:259–268) to generate pCGN549. HindIII-PstI digestion of pCN549 yielded a 3.1 kb fragment bearing the gentamicin resistance gene, which was made blunt ended by the Klenow fragment of DNA polymerase I and cloned into PvuII digested pBR322 (Bolivar et al., *Gene* (1977) 2:95–113) to create pBR322GM. pBR322GM was digested with DraI and SphI treated with Klenow enzyme to create blunt ends, and the 2.8 kb fragment cloned into the Ri origin-containing plasmid pLJbBll (Jouanin et al., *Mol. Gen. Genet.* (1985) 201:370–374) which has been digested with ApaI and made blunt ended with Klenow enzyme, creating pLHbBllGm. The extra ColEI origin and the kanamycin resistance gene were deleted from pLJBllGm by digestion with BamHI, followed by self-closure to create pGmBll. The HindIII site of pGBll was deleted by HindIII digestion, followed by treatment with Klenow enzyme and self-closure, creating pGmBll-H. The PstI site of pGmBll-H was deleted by PstI digestion, followed by treatment with Klenow enzyme and self-closure, creating pCGN1532.

(f) Final Construction of pCGN1578

The XhoI fragment of pCGN1546 containing the 35S promoter-Kan$^R$-tml-3' region was cloned into XhoI digested 1542b to create pCGN1556. The XhoI fragment from pCGN1546 was oriented within 1542b such that the order of components was: left border-35S promoter-Kan$^R$-tml-3'-lacZ'-right border.

The T-DNA containing 8gII fragment of pCGN1556 was cloned into BamHI restricted pCGN1532 resulting in the binary vector, pCGN1578. In pCGN1578, the orientation of the insert was such that the T-DNA left order was adjacent to the Ri plasmid origin of replication. This binary vector has several advantages, including a minimal amount of DNA between the T-DNA borders, high stability in Agrobacterium hosts, high copy number in *E. coli* hosts and blue/white screen with multiple restriction enzyme sites for ease of cloning target DNA.

EXAMPLE 6

Construction of Tagged Genomic Cassettes and Binary Vectors

The 2All genomic fragment was tagged with PG cDNA sense or antisense sequences. PG genomic DNA antisense sequences or DMA transferase (tmr) genomic DNA sequences in antisense or sense orientations. PG DNA sequences were inserted into the unique XbaI site of the pCGN1273 or the unique ClaI site of the pCGN1267 promoter cassettes. tmr sequences were inserted into the unique ClaI site of pCGN1261. A summary of the tagged genomic cassettes prepared is shown in Table 1 below. The inserted sequences will increase the size of the mRNA over the endogenous transcript, and thus the expression pattern of the construct can be compared to the endogenous gene by a single Northern hybridization in a manner analogous to the detection of a tuber specific potato gene described by Eckes et al., *Mol. Gen. Genet.* (1986) 205:14-22.

TABLE 1

Summary of Tagged Cassettes Constructed

| Genomic Clone Plasmid | "Tagged" Plasmid | Insertion | Orientation | Binary |
|---|---|---|---|---|
| pCGN1273 | pCGN1270 | PGcDNA | Sense | pCGN1268 |
| | pCGN1271 | PGcDNA | Antisense | pCGN1269 |
| | pCGN1215 | PG Genomic DNA | Antisense | pCGN1219/ pCGN1220 |
| pCGN1267 | pCGN1263 | PGcDNA | Sense | pCGN1260 |
| | pCGN1262 | PGcDNA | Antisense | pCGN1255/ pCGN1258 |
| | pCGN1225 | PG Genomic DNA | Antisense | pCGN1227/ pCGN1228 |
| | pCGN1266 | tmr Genomic DNA | Sense | pCGN1264/ pCGN1265 |

The preparation of the above tagged cassettes was as follows.

Isolation of Polygalacturonase Genomic Clone

An EcoRI partial genomic library established in Charon 4 constructed from DNA of a *Lycopersicon esculentum* cultivar was screened using a probe from polygalacturonase (PG) cDNA (Sheehy et al., *Mol. Gen. Genet.* (1987) 208:30-36). A lambda clone containing an approximately 16 kb insert was isolated from the library. An internal 2207 bp HindIII to EcoRI was sequenced. The HindIII-EcoRI fragment includes the PG promoter region.

Sequence of Genomic Clone

The DNA sequence of the genomic clone was determined by Sanger dideoxy techniques and is as shown in FIG. 5 of co-pending U.S. application Ser. No. 382,176 filed Jul. 19, 1989. The sequence of the genomic clone bases 1427 to 1748 are homologous to the PG cDNA sequence.

Preparation of pCGN1268 and pCGN1269 pCGN1273 was tagged with 383 bp (from base number -23 in the polylinker region to 360) from the 5' region of the tomato PG cDNA clone, F1 (Sheehy et al, *Mol. Gen. Genet.* (1987) 208:30-36), at the unique XbaI restriction enzyme site. The tag was inserted in the antisense orientation resulting in plasmid pCGN1271 and in the sense orientation yielding plasmid pCGN1270. Plasmids pCGN1270 and pCGN1271 were linearized at the unique BglII restriction enzyme site and cloned into the binary vector pCGN783 at the unique BamHI restriction enzyme site to yield pCGN1268 and pCGN1269 respectively.

Preparation of pCGN1219 and pCGN1220 pCGN1273 was tagged with a 0.5 kb fragment of DNA (base number 566 to 1055) from a PG genomic clone which spans the 5' end of the intron/exon junction. This fragment was cloned into the XbaI site resulting in plasmid pCGN1215. pCGN1215 was linearized at the unique BglII site and cloned into pCGN783 at the BamHI site resulting in two plasmids, pCGN1219 and pCGN1220, which differ only in the orientation of pCGN1215 in pCGN783.

Preparation of pCGN1255 and pCGN1258

The 383 bp XbaI fragment from the PG cDNA clone was cloned into the unique ClaI site of pCGN1267 after filling in the XbaI and ClaI ends with Klenow and blunt ligation. The fragment in a sense orientation resulted in plasmid pCGN1263 and in the antisense orientation gave pCGN1262. pCGN1263 was linearized at the unique BglII site and cloned into pCGN783 at the BamHI site yielding pCGN1260. pCGN1262 was also linearized at the BglII site and cloned into pCGN783 at the BamHI site resulting in two plasmids, pCGN1255 and pCGN1258, which differ only in the orientation of pCGN1262 in the binary vector pCGN783.

5 Preparation of pCGN1227 and pCGN1228

The 0.5 Kb fragment of the PG genomic clone spanning the intron/exon junction was cloned into pCGN1267 at the ClaI site in an antisense direction yielding plasmid pCGN1225. This plasmid was linearized at the BglII restriction enzyme site and cloned into pCGN783 at the BamHI site producing two plasmids, pCGN1227 and pCGN1228, which differ only in the orientation of pCGN1225 in the binary vector.

Preparation of pCGN1264 and pCGN1265

The Eco7 fragment (base numbers 5545 to 12,823) (Barker et al., *Plant Mol. Biol.* (1983) 2:335-350) from the octopine plasmid pTiA6 of *Agrobacterium tumefaciens* (Knauf and Nester, Plasmid (1982) 8:45-54) was subcloned into pUC19 at the EcoRI site resulting in plasmid pCGN71. A RsaI digest of pCGN71 allowed a fragment of DNA from bases 8487 to 9836 of the Eco7 fragment to be subcloned into the vector m13 BlueScript Minus (Stratagene, Inc.) at the SmaI site resulting in plasmid pCGN1278. This fragment contains the coding region of the genetic locus designated tmr which encodes a dimethylallyl transferase (isopentenyl transferase) (Akiyoshi et al., *Proc. Natl. Acad. Sci. USA* (1984) 81:5994-5998; Barry et al. (1984) 81:4776-4780). A mung bean exonuclease treatment (Promega Biotech) of pCGN1278 produced pCGN1272 in which there was a deletion on the 5' end of the tmr gene to a point 39 base pairs 5' of the start codon. The tmr gene from pCGN1272 was subcloned into the ClaI site of pCGN1267. The tmr gene, in the sense orientation, yielded plasmid pCGN1266. pCGN1266 was linearized at the BglII site and subcloned into pCGN783 at the BamHI site yielding two plasmids, pCGN1264 and pCGN1265, which differ only in the orientation of pCGN1266 in pCGN783.

EXAMPLE 7

Preparation of Transgenic Plants

Feeder plates were prepared by pipetting 0.5 ml of an eight day old suspension of *Nicotiana tabacum* cv xanthi cell suspension culture ($\sim 10^6$ cells/ml) onto 0.8% agar medium, containing MS salts, myo-inositol (100 mg/l), thiamine-HCl (1.3 mg/l), sucrose (30 g/l), potassium acid phosphate (200 mg/l) 2.4-D (0.2 mg/l), and kinetin (0.1 mg/l) (pH 5.5). The feeder cells were prepared at least 24 hours prior to use. A #1 Whatman sterile filter paper (Whatman Ltd, Maidstone, England) was placed on top of the tobacco feeder cells after the cells had been growing for at least 24 hours.

Agrobacteria containing the plasmid of interest were grown on AB medium: ($K_2HPO_4$, 3 gm/l; $NaH_2PO_4 \cdot H_2O$, 1.15 g/l $NH_4Cl$, 1 g/l; KCl 0.15 g/l; glucose, 5 g/l; $FeSO_4$, 0.25 mg/l; $MgSO_4$ 0.246 mg/l; $CaCl_2$, 0.14 mg/l; 15 g/l agar; gentamicin sulfate, 100 μg/l; and streptomycin sulfate, 100 μg/l) for 4-5 days. Single colonies were then inoculated into 5 ml of MG/L broth and preincubated overnight in a shaker (180 rpm) at 30° C.

Sterile tomato cotyledon tissue was obtained from 7-8 day old seedlings which had been grown at 24° C., with a 16 hr/8 hr day/night cycle in 100×25 mm petri dishes containing MSSV medium: Murashige-Skoog (MS) salts (#1117 Gibco Laboratories, New York), sucrose 30 g/l, Nitsch vitamins (Thomas, B.R., and Pratt, D. *Appl. Genet.* (1981) 59:215-219), 0.8% agar (pH 6.0). Any tomato species may be used as a tissue source, however, the inbred breeding line UC82B (Department of Vegetable Crops, University of California, Davis) is preferred. The tips and bases of the cotyledons were removed and the center section placed onto a feeder plate for a 24-hour preincubation period in a low light, generally about 40-50 micro-Einsteins, preferably less than 80 micro-Einsteins, at 24° C.

Following the preincubation period, the cotyledon explants were dipped into an agrobacteria suspension ($5 \times 10^8$ bacteria/ml) for approximately 5 minutes, blotted on sterile paper towels and returned to the original tobacco feeder plates. The explants were cocultivated with the agrobacteria for 48 hours on the tobacco feeder plates in low light (see above) at 24° C., then transferred to regeneration medium containing 500 mg/l of carbenicillin disodium salts and at least 100 mg/l of kanamycin sulfate. The regeneration medium is MS salts medium with zeatin (2 mg/l), myo-inositol (100 mg/l), sucrose (20 g/l), Nitsche vitamins and 0.8% agar (pH 6.0). After 10 days and subsequently every three weeks, the explants were transferred to fresh regeneration medium containing 500 mg/l of carbenicillin disodium salts and at least 100 mg/l of kanamycin sulfate. Shoots were harvested from 8 weeks onwards and placed on MSSV medium containing carbenicillin (50 mg/l), kanamycin (50 mg/l) and indole-3-butyric acid (1 mg/l). Roots developed in 7-14 days. Plants were then transplanted into soil.

An aminoglycoside phosphotransferase enzyme (APH3'II) assay is conducted on putative transformed tomato plants and shoots. APH3'II confers resistance to kanamycin and neomycin. APH3'II activity is assayed (Reiss et al., *Gene* (1984) 30:211-218) employing electrophoretic separation of the enzyme from other interfering proteins and detection of its enzymatic activity by in situ phosphorylation of kanamycin. Both kanamycin and [$\gamma$-$^{32}$P] ATP act as substrates and are embedded in an agarose gel which is placed on top of the polyacrylamide gel containing the proteins. After the enzymatic reaction, the phosphorylated kanamycin is transferred to P-81 phosphocellulose ion exchange paper and the radiolabeled kanamycin is finally visualized by autoradiography. The Reiss et al. method is modified in the final washing of the P-81 ion exchange paper by rinsing in 0.1 mg/ml of proteinase K.

EXAMPLE 8

Analysis of Expression Of Tagged Genomic Constructs in Transgenic Plants

Immature green fruit (approximately 3.2 cm in length) were harvested from two tomato plants cv. UC82B that had been transformed with a disarmed Agrobacterium strain containing pCGN1264. Transgenic plants are designated 1264-1 and 1264-11. The pericarp from two fruits from each plant was ground to a powder under liquid nitrogen, total RNA extracted, and polyA+mRNA isolated as described in Mansson et al., *Mol Gen. Genet.* (1985) 200:356-361. Young green leaves were also harvested from each plant and polyA+mRNA isolated.

Approximately 19 μg of total RNA from fruit, 7 ng of polyA+mRNA from fruit and 70 ng of polyA+mRNA from leaves from transformed plants 1264-1 and 1264-11 were run on a 0.7% agarose formaldehyde Northern gel and blotted onto nitrocellulose (Maniatis et al., Molecular Cloning: A Laboratory Manual (1982) Cold Spring Harbor, N.Y.). Also included on the gel, as a negative control, were approximately 50 ng of polyA+mRNA from leaf and immature green fruit of a nontransformed UC82B plant.

As a positive control, and to help in quantitating mRNA levels, in vitro transcribed RNA from pCGN1272 was synthesized using T3 polymerase (Stratagene, Inc.). Nineteen pg and 1.9 pg of this in vitro synthesized RNA were loaded onto the Northern gel.

The probe for the Northern filter was the 1.0 kb tmr insert DNA (a KpnI to SacI fragment) from pCGN1272 isolated by electroelution from an agarose gel (Maniatis, (1982) supra) and labeled by nick translation (Bethesda Research Laboratory kit) using $^{32}$p dCTP (Amersham).

The Northern filter was prehybridized at 42° C. for 5 hrs in the following solution: 25 ml Formamide, 12.5 ml 20×SSC, 2.5 ml 1 M NaP, 5 ml 50×Denhardts, 0.5 ml 10% SDS, 1 ml 250 mM EDTA, 1 ml 10 mg/ml ssDNA and 2 ml $H_2O$. Then one-fifth volume of 50% dextran sulfate and approximately 2.2×10⁷ cpm of the probe were added and hybridization was carried out for 15 hrs at 42° C. The Northern filter was washed one time in 2×SSC and 0.1% SDS at 55° C. and twice in 1X SSC and 0.1% SDS at 55° C. for 20 minutes each wash. The filter was allowed to air dry before being placed with Kodak XAR film and an intensifying screen at −70° C. for two days.

Northern Results on Transgenic Plants

The nicked tmr probe hybridized with a mRNA species approximately 1.7 Kb in length was observed in the total RNA and polyA+mRNA fruit lanes of the Northern blot. This is the expected length of the reintroduced 2All gene (0.7 Kb) tagged with the tmr gene (1.0 kb). The level of expression from the reintroduced tagged gene was somewhat lower than the level of expression from the endogenous 2All gene. The level of expression of the reintroduced gene in immature green fruit was higher than the expression level in leaf tissue, although there appeared to be a small amount of hybridizing mRNA in leaf tissue in these transformants.

EXAMPLE 9

2All Promoter Cassette

The 2All cassette contains 3.8 kb of DNA 5' of the transcriptional start site and the entire 3' region from the TGA stop codon to a site 2.0 kb 3' of the poly A addition site of the 2All gene. The 2All cassette was prepared as follows.

Transcriptional Initiation Region

The 5' end of the 2All cassette was constructed starting with an EcoRI subclone of the genomic clone as described in application PCT/US88/01811 cloned into the EcoRI site of Bluescript (+) (Stratagene) resulting in pCGN1288. This clone contains sequences from the EcoRI site at position 1651 in the intron of the 2All gene to the EcoRI site located 2.5 Kb upstream of the XhoI site at position 1 of the sequenced region. The XhoI fragment from position 1 of the sequenced region to the XhoI site in the Bluescript polylinker was deleted creating plasmid pCGN2004 which contains the 2All region from position 1 to position 1651. The coding region of 2All was deleted by treating this plasmid with ExonucleaseIII/S1 using the commercially available Erase-a-Base Kit (Promega Biotec) and sequencing deletion plasmids until one was found which had the coding region deleted to position 1366. The resulting plasmid, pCGN1251, had the genomic region from the XhoI site (position 1) to position 1366. The EcoRI fragment of pCGN1288 was then transferred to a chloramphenicol resistant plasmid vector, pCGN2015, to make pCGN1231. pCGN2015 is a Cm resistant derivative of the Bluescript plasmid. A BstEII/BamHI fragment of pCGN1251 was then transferred into BstEII/BamI digested pCGN1231 to make pCGN1235 which contains the region from the EcoRI site 2.5 kb upstream of the sequenced region) to position 1366 of the sequenced region flanked by the Bluescript polylinker in a Cm resistant vector.

Transcriptional and Translational Termination Region

The 3' end of the 2All cassette was constructed from pCGN1273 (described in application PCT/US88/01811) by digesting the plasmid with PvuI and EcoRI, isolating the 2249 bp insert (from position 2402 to 4653), ligating with a double-stranded oligonucleotide containing the sequence shown in FIG. 7 of co-pending U.S. application Ser. No. 382,176 filed Jul. 19, 1989, the BamHI sticky end to a PvuI sticky end, into a BlueScript vector which had been digested with BamHI and EcoRI. The resulting plasmid, pCGN1238 contains the 3' end of the 2All gene from the stop codon at position 2381 to the EcoRI site at position 4653.

Final Construction

Several versions of the 2All cassette in different vectors with different flanking restriction sites have been constructed. A cassette containing the 5' and 3' regions of the 2All gene was constructed by ligating the BamHI to EcoRV insert of pCGN1238 into pCGN1235 which had been digested with BamHI and XbaI (the XbaI site having been filled in with Klenow polymerase to make a blunt-ended fragment). The resulting plasmid, pCGN1240, has the 5' end of the 2All gene from the EcoRI site 2.5 kb upstream of the XhoI site (position 1) to position 1366 (which is located between the transcriptional initiation site of the 2All gene and the ATG), followed by a polylinker region (see FIG. 6 of co-pending U.S. application Ser. No. 382,176, filed Jul. 19, 1989, now abandoned,) with sites for SmaI, BamHI, PstI and SalI which can be conveniently used to insert genes, followed by the 3' region from position 2381 to 4653. The plasmid backbone of pCGN1240 is the Bluescript Cm plasmid.

Construction of Plasmid pCGN1241

A more convenient construct has the EcoRI of pCGN1240 excised and inserted into a Bluescript vector called pCGN1239 which has an altered polylinker region such that the entire cassette can be excised as a SacI-KpnI fragment. The altered BlueScript vector, pCGN1239, was constructed by modifying the BlueScript polylinker from the SacI site to the KpnI site including a synthetic polylinker with the following sequence: AGCTCGGTACCGAATTCGAGCTCGGTAC to create a polylinker with the following sites: SacI-KpnI-EcoRI-SacI-KpnI. The EcoRI insert of pCGN1240 was inserted into pCGN1239 to make pCGN1241.

Construction of pCGN2610 and pCGN2611

A Chloramphenicol resistant version of the 2All promoter cassette was constructed by inserting the synthetic polylinker described above (see construction of pCGN1241) into pCGN2015 to make pCGN1246, followed by insertion of the EcoRI fragment of pCGN1241 to make pCGN2610 and pCGN2611 which differ only by the orientation of the inserted fragment in the plasmid vector.

EXAMPLE 10

Comparison of Different Sized 2All 5' Regions

A beta-glucuronidase (GUS) reporter gene was used to evaluate the level of expression and tissue specificity of various 2All-GUS constructs. GUS is a useful reporter gene in plant systems because it produces a highly stable enzyme, there is little or no background (endogenous) enzyme activity in plant tissues, and the enzyme is easily assayed using fluorescent or spectrophotometric substrates. See, for example, Jefferson, *Plant Mol. Biol. Rep.* (1988) 5:387–405. Histochemical stains for GUS enzyme activity are also available which can be used to analyze the pattern of enzyme expression in transgenic plants. Jefferson (1988), supra.

Constructions containing 1.3 kb (short), 1.8 kb (intermediate length), or 3.8 kb (long) 2All 5' sequences fused to the GUS reporter gene were prepared. In addition, constructions were prepared which have altered 3' ends. The altered 3' ends are either a shorter 2All 3' end, or a 3' end from tr5 of the T-DNA of the Ti plasmid (Willmitzer et al. *Embo J.* (1982) 1:139-146; Willmitzer et al. *Cell* (1983) 42 1045-1056. The constructions were transferred to a binary vector (pCGN1578), and used in *A. tumefaciens* cocultivations. The resulting binary was used to transform tomato plants. The transgenic plants obtained were fluorometrically analyzed for GUS enzyme activity.

Preparation of Test Constructs

Construction of pCGN2601 and pCGN2602

These constructs contained 3.8 kb of 2All 5'GUS 2.4 kb of 2All 3' sequence, differing only in the orientation of the 2All/GUS construction with respect to the other elements of the binary vector plasmid. The constructs were made by inserting the PstI fragment of pRAJ260 (Jefferson, supra) into the PstI site of pCGN1240. The resulting plasmid, having the GUS gene in the sense orientation with respect to the 2All promoter, was named pCGN1242. The 2All/GUS construction was excised as an EcoRI fragment and cloned into the EcoRI site of pCGN1239 to make pCGN1247. The insert of pCGN1247 was then excised as a KpnI fragment and cloned into the KpnI site of the binary vector pCGN1578 to make pCGN2601 and pCGN2602. The orientation of the construction within the binary vector seemed to have no effect on expression of the DNA sequence of interest.

Construction of pCGN2812 pCGN2800 was constructed by deleting an XhoI fragment from pCGN1242. The resulting 2All/GUS construct, pCGN2800, containing 1.3 kb of 2All 5' sequence and 2.4 kb of 2All 3' sequence was linearized with KpnI and the entire plasmid was cloned into the KpnI site of the binary plasmid pCGN1578 to yield pCGN2812.

Construction of pCGN2816

A construction with 1.8 kb of 2All 5' sequence and 1.0 kb of 2All 3' sequence fused to the GUS reporter gene was made by digesting pCGN1242 with HindIII and cloning into the HindIII site of pCGN1578 to give pCGN2816.

Construction of pCGN2813 and pCGN2814 (2All 5'-GUS-Tr5 3' Constructs)

Two constructions were made in which the 3' sequence of 2All was replaced with the 3' terminator sequence of Tr5 of the T-DNA region of the Ti plasmid (Willmitzer et al., (1982), supra; Willmitzer et al., *Cell* (1983), 42:1045-1056). A Sau3A fragment from position 2396 to position 2920 of the T-DNA region of the Ti plasmid (Barker et al. (1983), supra) was cloned into the BamHI site of pUC18 (Norrander J. et al., *Gene* (1983) 26:101-106) to give pCGN9VK. A HindIII-SalI fragment of pCGN1242 was inserted into HindIII-SalI digested pCGN9VK to give pCGN2801 which has 1.8 kb of 2All 5' sequence and the transcript 5 3' sequence fused to the GUS reporter gene. In one case, the 2.0 kb HindIII fragment of pCGN1242 was also cloned in the proper orientation to give pCGN2802 which has 3.8 kb of 2All 5' and the transcript 5 3' end fused to the GUS reporter gene. These plasmids were each linearized with KpnI and cloned into the KpnI site of pCGN2813 (1.8 kb 2All 5') and pCGN2814 (3.8 kb 2All 5').

The completed binaries were used for cocultivation. *Agrobacterium tumefaciens* strain 2760 (also known as LBA4404, Hoekema et al., *Nature* (1983) 303:179-180) were transformed with the binary of interest using the method of Holsters et al. *Mol. Gen. Genet.* (1978) 163:181-187. The transformed binary was then used in the cocultivation of plants. Transgenic plants were prepared as set forth above.

Analysis of GUS Enzyme Activity

β-glucuronidase activity was measured using 4-methyl umbelliferyl glucuronide as substrate as outlined in Jefferson, *PMB Reporter* (1987) 5:387-405. In untransformed tomato leaves, the background enzyme levels were 5-10 pmol methyl umbelliferone (MU)/mg protein/min. Using the β-glucuronidase activity assay, timing of GUS expression under the control of a 3.8 kb 5' 2All sequence was evaluated at various developmental stages of tomato fruit. GUS enzyme activity was first detectable when the fruit began expanding, namely at approximately 13 days post-anthesis. Enzyme activity increased steadily throughout the fruit maturation stages (before ripening).

GUS enzyme activity was not seen in flower parts (unexpanded ovaries, stigma+style tissue, petals, sepals, or anthers) when transformants containing constructs with 3.8 kb of 2All 5' sequence such as pCGN2601 or pCGN2602 were analyzed. Some GUS enzyme activity was observed in leaf tissue, however. Surprisingly, an increased percentage of transformants in which GUS enzyme activity was not expressed in leaf but was expressed in fruit may be obtained through the use of the longer 2All 5' regions. Thus, sequences of up to about 1.3 kb upstream of the 2All promoter gave relatively high levels of expression in fruit but did not show optimal fruit-specific expression of inserted genes. Inclusion of an additional approximately 500 bp (the 1.8 kb 5' 2 All promoter) increased fruit-specificity but reduced levels of expression observed in the fruit.

Longer promoter constructions (3.8 kb 5' of the gene) gave a higher percentage of transgenic plants expressing the gene at high levels in the fruit as well as tighter control of fruit-specificity. For example, out of 30 pCGN2601/pCGN2602 (2All "long" promoter) transgenic plants analyzed, 27 (90%) showed the highest GUS enzyme activity in fruit and little or no detectable GUS enzyme activity in leaves. (One transformant did show GUS enzyme activity in leaf tissue at a level approximately twice background in leaf tissue. The level of enzyme activity in the fruit ranges up to greater than 100,000 pmol MU/mg protein/min. Background GUS enzyme activity in fruit is 50 to 100 pmol/MU/mg protein/min.

Approximately 35% (7/22) of the pCGN2812 (2All "short" promoter) transgenic plants showed high levels of GUS enzyme activity in the fruit, the levels being comparable to the levels observed with the "long", 3.8 kb 2All 5' region. However, 30% (14/24) of the plants containing the pCGN2812 construct also showed low levels of GUS activity in the leaves (levels are from 2× to 20× background leaf levels). Thus, some of the plants are expressing GUS in both leaves and fruit, some in fruit alone. None of the plants express GUS in leaves alone. The frequency of transgenic plants that expressed the 2All/GUS construct was lower when a shorter 5' end is used (35% vs. 90%) and the specificity of the expression is reduced: more plants were found that had measurable GUS activity in the leaf tissue. However, with the pCGN2812 construct, the level of expression in the fruit of plants that expressed the construct is as high as the levels obtained from the longer promoter.

None of the transgenic plants containing the intermediate length (1.8 kb) 5' end constructs showed any measurable GUS activity in leaves (CGN2813 (0/7); pCGN2816 (0/12)). However, in contrast to the results obtained with either the long (3.8 kb) promoter constructs or the short (1.3 kb) promoter constructs, none of the plants with the intermediate length (1.8 kb) promoter showed high levels of GUS enzyme activity in the fruit [pCGN2813 (0/5), pCGN2816 (0/19)]. The fruit from the pCGN2813 and pCGN2816 plants did show some GUS enzyme activity but the level was low in comparison to the high levels from the pCGN2812 plants.

From the foregoing, it is seen that the length of the 2All 5' region can influence the timing, level and tissue specificity of gene expression. The results suggest the influence of negative and positive expression modifiers in regions further upstream than the originally described 1.3 kb 2All 5' promoter region.

EXAMPLE 11

2All Constructs Comprising tmr

Construction of pCGN2612 and pCGN2613

The DMA transferase (tmr) gene from *A. tumefaciens* (Akiyoshi, et al. (1984) supra; Barry, et al. (1984) supra was inserted into the 2All cassette then transferred into a binary vector. The tmr gene was subcloned from the T-DNA (Barker, et al. (1983); base numbers 8,487-9,836) as an RsaI to RsaI fragment, pCGN1278. The upstream non-coding sequences were removed by ExoIII/mung bean deletion (Promega Biotec kit) followed by DNA sequencing to determine the exact endpoint of the deletion (pCGN1272). The deletion was to a point 39 base pairs upstream of the start codon for the DMA transferase gene. The region from 8,732 to 9,836 (Barker, et al. (1983) supra) was inserted into pCGN1240 at the SmaI site creating pCGN1249. The EcoRI fragment of pCGN1249 was excised and inserted into the EcoRI site of pCGN1239 to make pCGN2608. The insert from pCGN2608 was then excised with KpnI and inserted into the binary vector pCGN1578 to make pCGN2612 and pCGN2613 which differ only in the orientation of the 2All/tmr construction with respect to the other elements of the binary vector. The binary vectors are shown in FIG. 1.

2All-tmr Phenotypic Results

The majority of the transgenic plants containing the 2All-tmr constructs have a recognizable phenotype in the fruit. At green stages, the surface of the fruit had roughened appearance relative to normal fruit and sometimes appeared to be a more dusty green color than normal fruit. The altered phenotype was much more dramatic at the ripening stages when the fruit took on a mottled appearance: red in some areas, green in others. Cytokinins have been shown to delay or reverse senescence in plants (see, for example, Nooden and Leopole (1988), supra and references cited). Fruit ripening is often viewed as a senescence phenomenon so it is interesting to note that expression of a cytokinin-producing enzyme in ripening tomato fruit can alter the ripening process.

Northern Analysis

Northern Analysis of 1 T1 2All/tmr transgenic plant (2612-4) demonstrated that a tmr mRNA transcript of the proper length was produced. The mRNA accumulated to a level approximately 1000 fold lower than that of 2All RNA.

Analysis of offspring from 5 self-crosses of T1 transformants demonstrated a correlation between progeny which exhibited the blotchy fruit phenotype and those which expressed the kan gene. In three of the five families, the correlation between those plants which exhibited the blotchy phenotype and those which expressed the kan gene was nearly perfect. The blotchy phenotype was not observed in the original 2612-8 plant and was minimal in the original 2613-1 plant. The blotchy phenotype was not observed in kan negative plants. The correlation of kan gene segregation and fruit phenotype is shown in Table 2, below.

TABLE 2

Correlation Between Kan Gen Segregation And Fruit Phenotype

| Transformant | Germ. Assay Kan= /Kan − | Seedling Kan=/ Kan − | Fruit Phenotype = |
|---|---|---|---|
| 2613-4 (1:3) | 115:36 (3:1) | 21:4 (3:1) | 20:5 |
| 2612-4 | — | 24:1 | 22:1 |
| 2613-10 | 1:154 | 1:24 | 1:24 |
| 2612-8 (1:3?) | 124:37 (3:1) | 20:5 (3:1) | 2:19 |
| 2613-1 | 130:25 | 19:6 (3:1?) | 11:12 |

Cytokinin Expression

Cytokinin levels in fruit and leaf samples were measured in 1 T2 2All/tmr kan(+) transgenic plant (from 2613-4) and compared to levels in a null sibling. The analysis was performed on 0.5gm samples. The cytokinin levels were measured using a DDS analytical zeatin kit supplied by Danisco A/S (Copenhagen, Denmark) according to the manufacturers specifications. The literature enclosed with the cytokinin kit specifies that several cytokinins are measured in the ELISA assay part of the kit, including zeatin-N9-glucoside. At least two of these, zeatin riboside and zeatin are predicted products of tmr gene expression.

As shown in FIG. 2, higher levels of cytokinins were achieved in the kan(+) plant. Interestingly, cytokinin levels were higher in the ripe fruit parts than they were in areas that never ripened. The red and green patches on blotchy fruit both had more cytokinin than ripe fruit from the null sibling (23 pmol/gfw), with the red patches having a higher concentration of cytokinin (2265 pmol/gfw) than the green patches (317 pmol/gfw). This patchy phenomenon may be due to disturbance of a developmental switch in green fruit which signals the onset of ripening/fruit maturation. Some varieties may be more susceptible to this disturbance than others. As a result, these regions remain "young" in terms of color, cellular integrity, etc. as well as in patterns of gene expression. Therefore, the 2All promoter driving tmr gene expression in green patches is geared to lower levels of expression while the same chimeric gene construct in the red regions is responding to red ripe regulatory signals. The differences in the cytokinin concentrations between the red and green regions also appear to indicate that cytokinins are not readily transported between these different fruit regions.

A similar analysis of a kan(+) 2All/antisense tmr plant and its null sibling indicated that the kan(+) plant was also expressinq high levels of cytokinin in various fruit stages, significantly higher levels in fact than in the sense construct plant described above. Tests are underway to characterize this phenomena including consideration of the possibility that the gene construct in this plant might have been rearranged.

EXAMPLE 12

Preparation Of A pZ130 Expression Construct

Preparation of pCGN2901 and pCGN2902 pCGN2901 contains the region surrounding the pZ7-hydridizing region of the pZ130 genomic clone, including approximately 1.8 kb in the 5' direction and approximately 4 kb in the 3' direction. To prepare pCGN2901, Calgene Lambda 140 (FIG. 3) was digested with SalI and the resulting fragment which contained the pZ7-hydridizing region was inserted into pCGN2015, at the pCGN2015 unique SalI site, to create pCGN2901.

pCGN2902 contains the other SalI fragment (non-pZ7-hybridizing) of the pZ130 genome derived from SalI digestion of Calgene Lambda 140, also put into a pCGN2015 construct. pCGN2015 was prepared by digesting pCGN565 with HhaI, blunting with mung bean nuclease, and inserting the resulting fragment into an EcoRV digested BlueScriptKSM13- (Stratagene) vector to create pCGN2008. pCGN2008 was digested with EcoRI and HindIII, then blunted with Klenow. The 1156 bp chloramphenicol fragment was isolated. BlueScriptKSM13+(Stratagene) was digested with DraI and the resulting 2273 bp fragment isolated and ligated with the pCGN2008 chloramphenicol fragment creating pCGN2015.

Preparation Of A pZ130 Expression Construct

The pZ130 cassette contains 1.8 kb of DNA 5' of the translational start site and the 3'-region from the TAA stop codon to a site 1.2 kb downstream of the pZ130 gene. The pZ130 cassette was constructed as follows. Plasmid DNA isolated from pCGN2901 (see above) was digested to completion with NcoI and then treated with exonuclease isolated from mung bean (Promega, Madison, Wis.) to eliminate single-stranded DNA sequences, including the ATG sequence making up a portion of the NCOI recognition sequence. The sample was then digested to completion with SacI. The resulting 1.8 kb 5' SacI to NcoI fragment was then inserted into pCGN2015 (described above) to create pCGN2904. In order to eliminate redundant restriction enzyme sites and to make subsequent cloning easier, the plasmid DNA isolated from pCGN2904 was digested to completion with SalI and EcoRI and the resulting 1.8 kb fragment, containing the pZ130 5' sequences, was inserted into pBluescript 2 (Stratagene; LaJolla, Calif.) to create pCGN2907.

Plasmid DNA isolated from pCGN2901 was digested to completion with EcoRI and BamHI and the resulting 0.72 kb EcoRI to BamHI fragment located downstream (3') from the pZ130 coding region was inserted into pCGN2907 creating pCGN2908. Insertion of the 0.5 kb (approximately) DNA sequence including the pZ130 gene TAA stop codon and those sequences between the stop codon and the EcoRI site downstream (3'), and the addition of unique restriction sites to facilitate insertion of foreign genes, was accomplished as follows.

A polylinker/"primer" comprising the sequence 5'CGTTCCTGCAGCATGCCCGGGATC-GATAATAATTAAGTGAGG3' was synthesized to create a polylinker with the following sites: PstI-SphI-SmaI-ClaI and to include the pZ130 gene TAA stop codon as well as the following (3') 13 base pairs of the pZ130 gene 3' region sequence. Another oligonucleotide comprising the sequence 5'-CAAGAATT-CATAATATTATATATAC was synthesized to create a "primer" with an EcoRI restriction site and 16 base pairs of the pZ130 gene 3'-region immediately adjacent to the EcoRI site located approximately 0.5 kb 3' of the pZ130 gene TAA stop codon. The synthetic oligonucleotides were used in a polymerase chain reaction (PCR) in which plasmid DNA isolated from pCGN2901 was used as the substrate in a thermal cycler (Perkin-Elmer/Cetus, Norwalk, Conn.) as per the manufacturers instructions. The resulting 0.5 kb DNA product was digested to completion with PstI and EcoRI and the resulting 0.5 kb DNA fragment inserted into pCGN2908 to create pCGN2909. The complete DNA sequence of the 0.5 kb region from the PstI site to the EcoRI site was determined using the Sanger et al. (1971) dideoxy technique and verified that no mistakes in the sequence between the oligonucleotide primers had occurred during the PCR reaction.

The pZ130 cassette pCGN2909, thus comprises the 5' pZ130 DNA sequence from the SalI site at position 808 to position 2636 (see FIG. 3), unique PstI, SphI, and SmaI sites which can be conveniently used to insert genes, and the 3' pZ130 DNA sequences from the TAA stop codon at position 3173 (FIG. 3) through the BamHI site at position 4380. Using the GUS reporter gene to test ovary tissue expression, as described in Example 10, the tissue specificity of the ovary tissue promoter has been confirmed.

Analysis of Transgenic Plants

Transformed plants confirmed through a Southern analysis, containing the PZ130/tmr/ tmr constructs have been obtained. Fruit from the transformed plants do not show the blotchy phenotype observed in plants containing the 2All/tmr construct. The earlier expression profile of the pZ130 promoter may provide certain advantages for some cytokinin applications because the earlier expression provides a degree of improved uniformity in fruit cell expression, as compared with the results observed in Example 11.

The above results demonstrate the ability to identify developmentally regulated sequences in a plant genome, isolate the sequences and manipulate them. In this way, the production of transcription cassettes and expression cassettes can be produced which allow for differentiated cell production of the desired product. Thus, the phenotype of a particular plant part may be modified, without requiring that the regulated product be produced in all tissues, which may result in various adverse effects on the growth, health, and production capabilities of the plant. Particularly, fruit specific transcription initiation capability is provided for modifying the phenotypic properties of a variety of fruits to enhance properties of interest such as processing, organoleptic properties, storage, yield, or the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An expression cassette comprising:
in the 5'-3' direction of transcription, as operably joined components, a transcriptional and translational initiation region from a gene selected from the group consisting of 2All, Z130 and Z70, a DNA sequence encoding an enzyme in a cytokinin metabolic pathway, wherein transcription of said DNA sequence is regulated by said transcriptional initiation region, and a transcriptional termination region, wherein at least one of said initiation and termination regions is heterologous to said DNA sequence.

2. The expression cassette according to claim 1, wherein said metabolic pathway is a biosynthetic pathway.

3. The expression cassette according to claim 2, wherein said enzyme is DMA transferase.

4. A tomato plant cell comprising:
an expression cassette comprising, in the 5'-3' direction of transcription as operably joined components, a transcriptional and translational initiation region from a gene selected from the group consisting of 2All, Z130 and Z70, a DNA sequence encoding an enzyme in a cytokinin metabolic pathway, wherein said DNA sequence is under the transcriptional regulation of said transcriptional initiation region, and a transcriptional termination region, wherein at least one of said initiation and termination regions is heterologous to said DNA sequence.

5. The plant cell according to claim 4, wherein said enzyme is DMA transferase.

6. Tomato fruit comprising cells according to claim 5.

7. A method of modifying the phenotype of a tomato plant, said method comprising:

growing a tomato plant comprising cells transformed with an expression cassette comprising, in the 5'-3' direction of transcription as operably joined components, a transcriptional and translational initiation region from a gene selected from the group consisting of 2All, Z130 and Z70, a DNA sequence encoding an enzyme in a cytokinin metabolic pathway, wherein said DNA sequence is under the transcriptional regulation of said transcriptional initiation region, and a transcriptional termination region, wherein at least one of said initiation and termination regions is heterologous to said DNA sequence.

8. Tomato fruit having a modified phenotype produced by a plant obtained according to the method of claim 7.

9. The tomato fruit according to claim 8, wherein said modified phenotype comprises an increase in cytokinin in the cells of said fruit.

10. The tomato fruit according to claim 8, wherein said modified phenotype is increased solids.

11. A tomato fruit having a modified phenotype said fruit comprising:
plant cells containing an expression cassette comprising in the 5'→3' direction of transcription as operably joined components, a transcriptional and translational initiation region from a gene selected from the group consisting of 2All, Z130 and Z70, a DNA sequence encoding an enzyme in a cytokinin metabolic pathway, wherein transcription of said DNA sequence is regulated by said transcriptional initiation region, and a transcriptional termination region, wherein at least one of said initiation and termination regions is heterologous to said DNA sequence.

12. The tomato fruit according to claim 11, wherein said enzyme increases the level of cytokinin.

13. The tomato fruit according to claim 11, wherein said enzyme is DMA transferase.

14. The tomato fruit according to claim 12, wherein said modified phenotype is expressed uniformly in cells of said fruit.

15. The method of modifying the phenotype of a tomato plant according to claim 7, wherein said enzyme is DMA transferase.

16. A tomato plant comprising an expression cassette according to claim 1.

17. A tomato plant prepared according to the method of claim 15.

* * * * *